United States Patent
Hadlock et al.

(10) Patent No.: US 9,867,794 B2
(45) Date of Patent: *Jan. 16, 2018

(54) REGULATION OF OSTEOPONTIN

(71) Applicant: Pathologica LLC, San Francisco, CA (US)

(72) Inventors: Kenneth G. Hadlock, San Francisco, CA (US); Hope Lancero, Palo Alto, CA (US); Stephanie Yu, San Francisco, CA (US); Hien Kim Do, Palo Alto, CA (US)

(73) Assignee: Pathologica LLC, San Francisco, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 13/865,816

(22) Filed: Apr. 18, 2013

(65) Prior Publication Data

US 2013/0317113 A1 Nov. 28, 2013

Related U.S. Application Data

(63) Continuation of application No. 12/045,623, filed on Mar. 10, 2008, now Pat. No. 8,445,540.

(60) Provisional application No. 60/894,153, filed on Mar. 9, 2007.

(51) Int. Cl.
 *A61K 31/165* (2006.01)
 *A61K 31/155* (2006.01)

(52) U.S. Cl.
 CPC .................................. *A61K 31/155* (2013.01)

(58) Field of Classification Search
 None
 See application file for complete search history.

(56) References Cited

U.S. PATENT DOCUMENTS

| | | | |
|---|---|---|---|
| 4,201,788 A | 5/1980 | Russell et al. | |
| 5,580,715 A | 12/1996 | McGrath et al. | |
| 5,614,557 A | 3/1997 | Bey et al. | |
| 5,639,600 A | 6/1997 | McGrath et al. | |
| 5,744,122 A | 4/1998 | McGrath et al. | |
| 6,537,523 B1 | 3/2003 | McGrath et al. | |
| 6,544,541 B1 | 4/2003 | Zahradka | |
| 6,924,095 B2 | 8/2005 | McGrath et al. | |
| 7,087,648 B1 | 8/2006 | McGrath | |
| 7,198,946 B2 | 4/2007 | Marton et al. | |
| 7,445,794 B1 | 11/2008 | Newell et al. | |
| 7,754,765 B2 | 7/2010 | Wang et al. | |
| 7,879,914 B2 | 2/2011 | McGrath et al. | |
| 8,258,186 B2 | 9/2012 | McKearn et al. | |
| 8,445,540 B2 | 5/2013 | Hadlock et al. | |
| 8,609,734 B2 | 12/2013 | McKearn et al. | |
| 8,858,991 B2 | 10/2014 | McKearn et al. | |
| 2003/0130357 A1* | 7/2003 | Ramesh et al. | 514/674 |
| 2003/0175832 A1 | 9/2003 | Marton et al. | |
| 2005/0159493 A1 | 7/2005 | McGrath et al. | |
| 2005/0256207 A1 | 11/2005 | McGrath et al. | |
| 2006/0160087 A1 | 7/2006 | McGrath et al. | |
| 2007/0078187 A1 | 4/2007 | McGrath et al. | |
| 2008/0262092 A1 | 10/2008 | Hadlock et al. | |
| 2009/0017114 A1 | 1/2009 | Heasley et al. | |
| 2011/0091418 A1 | 4/2011 | McGrath et al. | |
| 2011/0112199 A1 | 5/2011 | McKearn et al. | |
| 2012/0219970 A1 | 8/2012 | McGrath | |
| 2012/0269891 A1 | 10/2012 | McKearn et al. | |
| 2012/0289604 A1 | 11/2012 | McKearn et al. | |
| 2013/0317113 A1 | 11/2013 | Hadlock et al. | |
| 2014/0051765 A1 | 2/2014 | McKearn et al. | |
| 2014/0187643 A1 | 7/2014 | McKearn et al. | |
| 2015/0359761 A1 | 12/2015 | Blitzer et al. | |

FOREIGN PATENT DOCUMENTS

| | | |
|---|---|---|
| EP | 2283830 A1 | 2/2011 |
| WO | 199621450 A2 | 7/1996 |
| WO | 199921542 A2 | 5/1999 |
| WO | 20074742 A1 | 12/2000 |
| WO | 2003089601 A2 | 10/2003 |
| WO | 2006091522 A2 | 8/2006 |
| WO | 2007016338 A2 | 2/2007 |
| WO | 2007035957 A2 | 3/2007 |
| WO | 2008112659 A2 | 9/2008 |
| WO | 2009018368 A1 | 2/2009 |
| WO | 2011009039 A2 | 1/2011 |
| WO | 2012100043 A2 | 7/2012 |
| WO | 2014110154 A1 | 7/2014 |
| WO | 2005041988 A1 | 5/2015 |

OTHER PUBLICATIONS

Guo X et al., "Spermidine alleviates severity of murine experimental autoimmune encephalomyelitis," *Invest Ophthalmol Vis Sci*, Apr. 1, 2011, 52(5):2696-703.
Chabas D et al., "The Infuence of the Proinfammatory Cytokine, Osteopontin, on Autoimmune Demyelinating Disease," *Science*, Nov. 23, 2001, 294(5547):1731-5.
Ackerman, J. et al., Drugs Affecting the Cell Cycle via Actions on the Polyamine Metabolic Pathway, Progress in Cell Cycle Res. 5, 461-468, 2003.
Allan, A. et al., Role of the Integrin-Binding Protein Osteopontin in Lymphatic Metastasis of Breast Cancer, Am J Pathol. 169(1), 233-246, 2006.
Ang, C. et al., Plasma Osteopontin Levels are Predictive of Disease Stage in Patients With Transitional Cell Carcinoma of the Bladder, BJU Int. 96, 803-805, 2005.
Banerjee, S. et al., Gene Expression Profiling in Inflammatory Airway Disease Associated With Elevated Adenosine, Am J Physiol Lung Cell Mol Physiol. 282, 169-182, 2002.

(Continued)

*Primary Examiner* — Craig Ricci
(74) *Attorney, Agent, or Firm* — Cynthia Hathaway; Dennis A. Bennett

(57) ABSTRACT

The present invention provides methods for the regulation of osteopontin activity in a subject as well as for treating or preventing conditions associated with an increased activity of osteopontin activity in a subject.

1 Claim, 16 Drawing Sheets

(56) References Cited

OTHER PUBLICATIONS

Bao, L. et al., Osteopontin in Metastatic Lesions as a Prognostic Marker in Ovarian Cancers, J Biomed Sci. 14, 373-381, 2007.
Birnbaum, G., Long-Term Disease-Modifying Therapies, Multiple Sclerosis, Ch. 8, 1-18, 2009.
Bonvini, JM et al., Lack of in Vivo Function of Osteopontin in Experimental Anti-GBM Nephritis, J Am Sac Nephrol. 11, 1647-1655, 2000.
Bramwell, V. et al., Serial Plasma Osteopontin Levels Have Prognostic Value in Metastatic Breast Cancer, Clin Cancer Res. 12(11), 3337-3343, 2006.
Brown , L. et al., Osteopontin Expression and Distribution in Human Carcinomas, Am J Pathol 145(3), 610-623, 1994.
Bruemmer, D. et al., Angiotensin II—Accelerated Atherosclerosis and Aneurysm Formation is Attenuated in Osteopontin-Deficient Mice, J Clin Invest. 112(9), 1318-1331, 2003.
Chambers, A. et al., Osteopontin Expression in Lung Cancer, Lung Cancer 15, 311-323, 1996.
Chiocchetti, A. et al., High Levels of Osteopontin Associated with Polymorphisms in its Gene are a Risk Factor for Development of Autoimmunity/Lymphoproliferation, Blood 103(4), 1376-1382, 2004.
Coppola, D. et al., Correlation of Osteopontin Protein Expression and Pathological Stage Across a Wide Variety of Tumor Histologies, Clin Cancer Res. 10, 184-190, 2004.
Cronstein, B., Low-Dose Methotrexate: A Mainstay in the Treatment of Rheumatoid Arthritis, Pharm Revs. 57(2), 163-172, 2005.
Della Ragione, F. et al., Effect of Analogues of 5'-Methylthioadenosine on Cellular Metabolism, Biochem J. 210, 429-435, 1983.
Denhardt, D. et al., Role of Osteopontin in Cellular Signaling and Toxicant Injury, Annu Rev Pharmacol Toxicol. 41, 723-749, 2001.
Ekelund, S. et al., Guanidino-Containing Drugs in Cancer Chemotherapy: Biochemical and Clinical Pharmacology, Biochem Pharmacol. 61, 1183-1193, 2001.
EP 2121586 Extended European Search Report, dated Jul. 22, 2011.
EP 2453886 Extended European Search Report, dated Nov. 5, 2012.
Fedarko, N. et al., Elevated Serum Bone Sialoprotein and Osteopontin in Colon, Breast, Prostate, and Lung Cancer, Clin Cancer Res. 7, 4060-4066, 2001.
Fischer, D. et al., A Role for Adenosine Deaminase in Human Monocyte Maturation, J Clin Invest. 58, 399-407, 1976.
Freedlander, BL et al., Carcinostatic Action of Polycarbonyl Compounds and Their Derivatives II. Glyoxal Bis (Guanylhydrazone) and Derivatives, Cancer Res. 18, 360-363, Apr. 1958.
Freedlander, BL et al., Carcinostatic Action of Polycarbonyl Compounds and Their Derivatives III. Hydroxymethylglyoxal Bis (Guanylhydrazone), Cancer Res. 18, 1286-1289, Dec. 1958.
Freireich, E. et al., Methylglyoxal Bis (Guanylhydrazone): A New Agent Active Against Acute Myelocytic Leukemia, Cancer Chemotherapy Reports 16, 183-186, 1962.
Furger, K. et al., The Functional and Clinical Roles of Osteopontin in Cancer and Metastasis, Curr Mol Med. 1(5), 621-632, 2001.
Hadjimichael, O. et al., Persistent Pain and Uncomfortable Sensations in Persons With Multiple Sclerosis, Pain 127, 35-41, 2007.
Harth, M. et al., Monocyte Dependent Excited Oxygen Radical Generation in Rheumatoid Arthritis: Inhibition by Gold Sodium Thiomalate, J Rheumatol 10(5), 701-707, 1983.
Hasko, G. et al., Shaping of Monocyte and Macrophage Function by Adenosine Receptors, Pharmacol Ther. 113(2), 264-275, 2007.
Herr, H. et al., Phase I Trial of Alpha-Difluoromethyl Ornithine (DFMO) and Methylglyoxal Bis (Guanylhydrazone) (MGBG) in Patients With Advanced Prostatic Cancer, Urology 28(6), 508-511, 1986.
Hershfield, M., New Insights Into Adenosine-Receptor-Mediated Immunosuppression and the Role of Adenosine in Causing the Immunodeficiency Associated With Adenosine Deaminase Deficiency, Eur J Immunol. 35, 25-30, 2005.
Hibasami, H. et al., Studies of Inhibition of Rat Spermidine Synthase and Spermine Synthase, Biochem J. 187, 419-428, 1980.
Huang, Y. et al., Molecular Mechanisms of Polyamine Analogs in Cancer Cells, Anti-Cancer Drugs 16, 229-241, 2005.
Hur, EM et al., Osteopontin-Induced Relapse and Progression of Autoimmune Brain Disease Through Enhanced Survival of Activated T Cells, Nature Immunol. 8(1), 74-83, 2007.
Jensen, B. et al., Dialyzability of Methyl-GAG, Cancer Treat Rep. 67, 283-284, 1983.
Kamatani, N. et al., Dependence of Adenine Production Upon Polyamine Synthesis in Cultured Human Lymphoblasts, Biochim Biophys Acta 675, 344-350, 1981.
Kaminska, J. et al., Pretreatment Serum Levels of Cytokines and Cytokine Receptors in Patients With Non-Small Cell Lung Cancer, and Correlations With Clinicopathological Features and Prognosis, Oncology 70, 115-125, 2006.
Kawamura, K. et al., Differentiation, Maturation, and Survival of Dendritic Cells by Osteopontin Regulation, Clin Diagn Lab Immunol. 12(1), 206-212, 2005.
Kelsen, D. et al., Phase II Trials of Methylglyoxal-bis (Guanylhydrazone), Am J Clin Oncol 5, 221-225, 1982.
Kim, JH et al., Osteopontin as a Potential Diagnostic Biomarker for Ovarian Cancer, JAMA 287(13), 1671-1679, 2002.
Liaw, L et al., Altered Wound Healing in Mice Lacking a Functional Osteopontin Gene (spp1), J Clin Invest. 101(7), 1468-1478, 1998.
Lieber, C. et al., S-Adenosylmethionine: Molecular, Biological, and Clinical Aspects—An Introduction, Am J Clin Nutr 76(suppl), 1148S-1150S, 2002.
Liesmann, J. et al., Pharmacokinetics of Methyl-Gloxyl Bis-Guanylhydrozone (MGBG), AACR Abstracts 605, 151, 1980.
Maddox, AM et al., Polyamines Increase in Human Peripheral Blood and Bone Marrow Mononuclear Cells Following Administration of Methylglyoxal Bis(Guanylhydrazone), Chemotherapy 34, 419-429, 1988.
Matsui, Y. et al., Osteopontin Deficiency Attenuates Atherosclerosis in Female Apolipoprotein E-Deficient Mice, Arterioscler Thromb Vasc Biol. 23, 1029-1034, 2003.
Maubec, E. et al., Subcutaneous Inflammatory Edema Induced by MINE Chemotherapy, Ann Dermatol Venereal. 128(4), 534-537, 2001.
Mazzali, M. et al., Osteopontin—A Molecule for All Seasons, QJM 95, 3-13, 2002.
Messina, L. et al., Polyamine Involvement in Functional Activation of Human Macrophages, J Leukoc Biol. 52, 585-587, 1992.
Mezzano, S. et al., Overexpression of Chemokines, Fibrogenic Cytokines, and Myofibroblasts in Human Membranous Nephropathy, Kidney Int. 57, 147-158, 2000.
Mihich, E. et al., Anti-Tumor Effects and Toxicology of Methylglyoxal Bis (Guanylhydrazone), Proc Nat Acad Sciences Abstracts, 43, 1959.
Mihich, E., Current Studies With Methylglyoxal-Bis (Guanylhydrazone), Cancer Res. 23, 1375-1389, 1963.
WO 2008/112659 IPRP, dated Sep. 15, 2009.
WO 2011/009039 Publication, Jan. 20, 2011.
WO 2011/009039 International Search Report, dated Apr. 27, 2011.
WO 2011/009039 Written Opinion, Jan. 16, 2012.
WO 2011/009039 IPRP, dated Jan. 17, 2012.
WO 2012/100043 Publication, Jul. 26, 2012.
WO 2012/100043 International Search Report, dated Aug. 16, 2012.
WO 2012/100043 Written Opinion, dated Jul. 19, 2013.
WO 2012/100043 IPRP, dated Jul. 23, 2013.
WO 2014/110154 Publication, Jul. 17, 2014.
WO 2014/110154 International Search Report, dated Jul. 17, 2014.
WO 2014/110154 Written Opinion, dated Jul. 8, 2015.
WO 2014/110154 IPRP, dated Jul. 14, 2015.
www.metrohealth.org (accessed online May 18, 2009).
Mor, G. et al., Serum Protein Markers for Early Detection of Ovarian Cancer, PNAS 102(21), 7677-7682, 2005.
Nemir, M. et al., Targeted Inhibition of Osteopontin Expression in the Mammary Gland Causes Abnormal Morphogenesis and Lactation Deficiency, J Biol Chem. 275(2), 969-976, 2000.
Noiri, E et al., Reduce Tolerance to Acute Renal Ischemia in Mice With a Targeted Disruption of the Ostepontin Gene, Kidney Int. 56, 74-82, 1999.
NZ 597488 Examination Report, dated Aug. 8, 2012.

(56) References Cited

OTHER PUBLICATIONS

Oates, A. et al., The Identification of Osteopontin as a Metastasis-Related Gene Product in a Rodent Mammary Tumour Model, Oncogene 13, 97-104, 1996.
Ohmori, R. et al., Plasma Osteopontin Levels Are Associated With the Presence and Extent of Coronary Artery Disease, Atherosclerosis 170, 333-337, 2003.
Okada, H. et al., Tubular Osteopontin Expression in Human Glomerulonephritis and Renal Vasculitis, Am J Kidney Dis. 36(3), 498-506, 2000\.
Oliverio, V. et al., The Distribution, Excretion, and Metabolism of Methylglyoxal-Bis-Guanylhydrazone-C14, Clin Pharmacol and Experimental Thera Ser. 141, 149-156, 1963\.
Panzer, U. et al., Monocyte Chemoaffractant Protein-1 and Osteopontin Differentially Regulate Monocytes Recruitment in Experimental Glomerulonephritis, Kidney Int. 59, 1762-1769, 2001.
Pixley, F. et al., Protein Tyrosine Phosphatase Phi Regulates Paxillin Tyrosine Phosphorylation and Mediates Colony-Stimulating Factor 1-Induced Morphological Changes in Macrophages, Mol Cell Biol. 21(5), 1795-1809, 2001.
Pixley, F. et al., CSF-1 Regulation of the Wandering Macrophage: Complexity in Action, Trends Cell Biol. 14(11), 628-638, 2004.
Regelson, W. et al., Initial Clinical Study of Parenteral Methylglyoxal Bis (Guanylhydrazone) Diacetate, Cancer Chemother Repts. 11, 81-86, 1961.
Regelson, W. et al., Clinical Experience With Methylglyoxal Bis (Guanylhydrazone) Dihydrochloride: A New Agent With Clinical Activity in Acute Myelocytic Leukemia and the Lymphomas, Cancer Chemother Repts. 27, 15-26, 1963.
Renkl, A. et al., Osteopontin Functionally Activates Dendritic Cells and Induces Their Differentiation Toward a Th1- Polarizing Phenotype, Blood 106(3), 946-955, 2005.
Rittling, S. et al., Osteopontin Function in Pathology Lessons from Osteopontin-Deficient Mice, Exp Nephrol. 7, 103-113, 1999.
Rudland, P. et al., Prognostic Significance of the Metastasis-Associated Protein Osteopontin in Human Breast Cancer, Cancer Res. 62, 3417-3427, 2002.
Sakaguchi, H. et al., Clinical Implications of Osteopontin in Metastatic Lesions of Uterine Cervical Cancers, Cancer Lett. 247, 98-102, 2007.
Salvi, M. et al., The Effect of Methylglyoxal-Bis (Guanylhydrazone) on Mitochondrial Ca2+ Fluxes, Biochem Pharmacol. 63, 247-250, 2002.
Sato, T. et al., Osteopontin/Eta-1 Upregulated in Crohn's Disease Regulates the Th1 Immune Response, Gut 54, 1254-1262, 2005.
Siimes, M. et al., Synergistic Action of Two Polyamine Antimetabolites Leads to a Rapid Therapeutic Response in Childhood Leukemia, Int J Cancer 28, 567-570, 1981.
Simon, M. et al., Phase II Trial of Methylglyoxal Bis-Guanylhydrazone (MGBG) in Refractory Small Cell Lung Cancer, Invest New Drugs 8; S79-S81, 1990.
Takami, J. et al., Experimental Chronochemotherapy With Methylglyoxal Bis-(Guanylhydrazone) (Methyl-GAG), AACR Abstracts 882, 223, 1981.
U.S. Appl. No. 14/033,738, Non-Final Office Action, dated Apr. 7, 2015.
U.S. Appl. No. 14/033,738, Final Office Action, dated Sep. 15, 2015.
U.S. Appl. No. 14/063,541, Non-Final Office Action, dated Dec. 27, 2013.
U.S. Appl. No. 14/063,541, Non-Final Office Action, dated Aug. 14, 2014.
U.S. Appl. No. 14/063,541, Applicant-Initiated Interview Summary, Dec. 16, 2014.
U.S. Appl. No. 14/063,541, Final Office Action, dated May 5, 2015.
U.S. Appl. No. 14/063,541, Affidavit-Traversing Rejections or Objections Rule 132, Nov. 5, 2015.
U.S. Appl. No. 14/458,919, Non-Final Office Action, dated Apr. 6, 2015.
U.S. Appl. No. 14/458,919, Affidavit-Traversing Rejections or Objections Rule 132, dated Oct. 6, 2015.
U.S. Pat. No. 8,258,186, Non-Final Office Action, dated Apr. 5, 2012.
U.S. Pat. No. 8,258,186, Applicant Initiated Interview Summary, dated May 16, 2012.
U.S. Pat. No. 8,258,186, Notice of Allowance, dated Jun. 14, 2012.
U.S. Pat. No. 8,445,540, Non-Final Office Action, dated May 27, 2009.
U.S. Pat. No. 8,445,540, Final Office Action, dated Apr. 1, 2010.
U.S. Pat. No. 8,445,540, Notice of Allowance, dated Jan. 22, 2013.
U.S. Pat. No. 8,609,734, Non-Final Office Action, dated Dec. 4, 2012.
U.S. Pat. No. 8,609,734, Applicant-Initiated Interview Summary, dated Dec. 12, 2013.
U.S. Pat. No. 8,609,734, Notice of Allowance, dated Aug. 2, 2013.
U.S. Pat. No. 8,858,991, Non-Final Office Action, dated May 9, 2013.
U.S. Pat. No. 8,858,991, Applicant-Initiated Interview Summary, dated Dec. 23, 2013.
U.S. Pat. No. 8,858,991, Examiner-Initiated Interview Summary, dated Feb. 21, 2014.
U.S. Pat. No. 8,858,991, Final Office Action, dated Feb. 21, 2014.
U.S. Pat. No. 8,858,991, Examiner-Initiated Interview Summary, dated Feb. 25, 2014.
U.S. Pat. No. 8,858,991, Notice of Allowance, dated Jun. 9, 2014.
White, F., Methyl-GAG, Cancer Chemother Repts. 24, 79-84, 1962.
WO 2008/112659 Publication, Sep. 18, 2008.
WO 2008/112659 International Search Report, dated Nov. 20, 2008.
WO 2008/112659 Written Opinion, dated Sep. 9, 2009.
Gilgun-Sherki, Y. et al., The Role of Oxidative Stress in the Pathogenesis of Multiple Sclerosis: The Need for Effective Antioxidant Therapy, J Neurol 251: 261-268, 2004.
Lovaas, E., Antioxidative and Metal-Chelating Effects of Polyamines, Advances in Pharmacology 38: 119-149, 1997.
Murugaiyan, G. et al., Increased Osteopontin Expression in Dendritic Cells Amplifies IL-17 Production by CD4+ T Cells in Experimental Autoimmune Encephalomyelitis and in Multiple Sclerosis, J Immunol 181(11): 7480-7488, 2008.
Zhang, M. et al., Spermine Inhibition of Monocyte Activation and Inflammation, Molecular Medicine 5: 595-605, 1999.
Marton, et al., Ann. Rev. Pharm. Toxicol., (1995), 35, 55-91.
Wallace, et al., Amino Acids, (2003), 26, 353-365.
Kaczmarek, et al., Cancer Res., (1992), 52, 1891-1894.
Dunzendorfer, U., et al, Some Aspects of Clearance of Mitoguazone in Cancer Patients and Experimental Cancer Models, Drug Res., (1986), 36, 506-508.
Mihich, E., Pharmacology of Methylglyoxal-bis-(guanylhydrazone) (CH3-G), Cancer Research, (1962), 22, 962-974.
Levin, Robert H., Different Patterns of Remission in Acute Myelocytic Leukemia: A Comparison of the Effects of Methyl-Glyoxal-Bix-Guanylhydrazone and 6-Mercaptopurine, Blood, (1963), 21, 6, 689-698.
Andrea Manni et al., (2004) Cellular mechanisms mediating the anti-invasive properties of the ornithine decarboxylase inhibitor [alpha]-difluoromethylornithine (DFMO) in human breast cancer cells,Clinical & Experimental Metastasis ; Official Journal of the Metastasis Research Society, vol. 21, No. 5, 1, pp. 461-467.
Giannessi F., (2003) "Carnitin E Palmitoyltransferase INH Ibitors in the Management of Type 2 Diabetes: An Old Promise to be Maintained", Drugs of the Future, Prous Science, ES, vol. 28, No. 4, 1, pp. 371-381.
Von Hoff D D. et al., (1990) "M~thylglyoxal bis-guanylhydrazOfle in advanced bladder cancer". European Journal of Cancer and Clinical Oncology, Oxford, GB, vol. 26, No. 7, Jan. 1, 1990 (Jan. 1, 1990), p. 848.
Lim S W et al: "MGBG Therapy of Relapsed Extralymphatic, i HIV-Associated Non-Hodgkin'S Lymphoma (H IV NHL)", Proceedings. American Society of Clinical Oncology, Meeting, Waverly Press, Baltimore, MD, US, vol. 14, Mar. 1, 1995 (Mar. 1, 1995), p. AI 274.
Seiler N. et al., Polyamines and apoptosis. J Cell Mol Med. 9(3):623-642, 2005 J Cell Mol Med. Jul.-Sep. 2005;9 (3):623-42.

(56) References Cited

OTHER PUBLICATIONS

Sherr CJ et al., The FMS gene and the CSF-1 receptor. Cancer Surv. 5(2):221-32 (1986).

Shevde LA et al., Osteopontin knockdown suppresses tumorigenicity of human metastatic breast carcinoma, MDA-MB-435. Clin Exp Metastasis 23(2):123-33 (2006).

Singh RP et al., Definition of a specific interaction between the early T lymphocyte activation 1 (Eta-1) protein and murine macrophages in vitro and its effect upon macrophages in vivo. J Exp Med. 171(6):1931-42 (1990).

Standal T et al., Role of osteopontin in adhesion, migration, cell survival and bone remodeling. Exp Oncol. 26 (3):179-84 (2004).

Thiele, Annalen Der Chemie 302:275-290, 1898.

Tushinski RJ et al., The regulation of mononuclear phagocyte entry into S phase by the colony stimulating factor CSF-1. J Cell Physiol. 122(2):221-8 (1985).

Vogt MH et al., Elevated osteopontin levels in active relapsing-remitting multiple sclerosis. Ann Neurol. 53(6):819-22 (2003).

Wallace HM et al., Inhibitors of polyamine metabolism: review article. Amino Mids. 26(4):353-65 (2004).

Webb SE et al., Direct observation and quantification of macrophage chemoattraction to the growth factor CSF-1. J Cell Sci. 109:793-803 (1996).

Weber GF et al., Phosphorylation-dependent interaction of osteopontin with its receptors regulates macrophage migration and activation. J Leukoc Biol. 72(4):752-61 (2002).

Wong CK et al., Elevation of plasma osteopontin concentration is correlated with disease activity in patients with systemic lupus erythematosus. Rheumatology (Oxford). 44(5):602-6 (2005).

Xu G et al., Role of osteopontin in amplification and perpetuation of rheumatoid synovitis. J Clin Invest. 115(4):1060-7 (2005).

Yoshitake H et al., Osteopontin-deficient mice are resistant to ovariectomy-induced bone resorption. PNAS 96:8156-60 (1999).

Yu XQ et al., A functional role for osteopontin in experimental crescentic glomerulonephritis in the rat. Proc Assoc Am Physicians. 110(1):50-64 (1998).

Zhang JG et al., The role of adenosine A2A and A2B receptors in the regulation of TNF-alpha production by human monocytes. Biochem Pharmacol. 69(6):883-9 (2005).

Zhiyong M et al., Differential osteopontin expression in phenotypically distinct subclones of murine breast cancer cells mediates metastatic behavior. J Biol Chem. 279(45):46659-67 (2004).

Zhong J et al., Osteopontin deficiency protects mice from Dextran sodium sulfate-induced colitis. Inflamm Bowel Dis. 12(8):790-6 (2006).

Bitonti AJ et al., Characterization of Trypanosoma brucei brucei S-adenosyl-L-methionine decarboxylase and its inhibition by Berenil, pentamidine and methylglyoxal bis(guanylhydrazone). Biochem J. 237(3):685-9 (1986).

Regenass U et al., CGP 48664, a new S-adenosylmethionine decarboxylase inhibitor with broad spectrum antiproliferative and antitumor activity. Cancer Res. 54(12):3210-7 (1994).

Boeshore KL et al., Novel changes in gene expression following axotomy of a sympathetic ganglion: A microarray analysis. J Neurobiol. 59:216-235 (2004).

Manni A et al., Cellular mechanisms mediating the anti-invasive properties of the ornithine decarboxylase inhibitor a-difluoromethylornithine (DFMO) in human breast cancer cells. Clin Exp Metast. 21:461-467 (2004).

Takahashi F et al., Osteopontin is induced by nitric oxide in RAW 264.7 cells. IUBMB Life. 49:217-221 (2000).

\* cited by examiner 1,1'[methylethanediylidenedinitrilo]diguanidine
Methylglyoxal bis(guanyl-hydrazone) or MGBG N,N'-bis(3-ethylaminopropyl)-cis-but-2-ene-1,4-diamine
SL11047 or SL47

$N^1,N^{1'}$-(cyclopropane-1,2-diylbis(methylene))bis($N^4$-ethylbutane-1,4-diamine)
SL11093 or SL93

PA001 treatment of SIV infected macaques results in depletion of infected macrophages in CNS

REGULATION OF OSTEOPONTIN

CROSS-REFERENCE TO RELATED APPLICATIONS

This application claims priority to, and is a continuation of U.S. application Ser. No. 12/045,623, filed Mar. 10, 2008, which claims priority to Provisional Application Ser. No. 60/894,153, entitled "Regulation of Osteopontin," filed Mar. 9, 2007, each of which is incorporated herein by reference in their entirety.

Osteopontin ("OPN"), also known as secreted phosphoprotein 1 ("SPP1"), early T-lymphocyte activation marker ("Eta-1"), sialoprotein 1 or 44K BPP (bone phosphoprotein), is a glycosylated phosphoprotein found in plasma, other bodily fluids, and extracellular matrices. The protein is composed of approximately 300 amino acids residues and has about 30 carbohydrate residues, including 10 sialic acid residues, attached to it. OPN is an acidic protein which exhibits a high amino acid homology between species (e.g., mouse, rat, human and pig) with several conserved elements including a stretch of 7 to 9 Asp or Glu residues.

Osteopontin is biosynthesized by a variety of tissue types including preosteoblasts, osteoblasts, osteocytes, extraosseous cells in the inner ear, brain, kidney, deciduum, placenta, odontoblasts, some bone marrow cells, hypertrophic chondrocytes, macrophages, smooth muscle, and endothelial cells. In the bone, the protein is primarily made by cells of the osteoblastic lineage and deposited on mineralized matrix. It is abundant in bone mineral matrix and accelerates bone regeneration and remodeling. Osteopontin is a multifunctional protein with an ability to bind several proteins, including integrin proteins and variants of the protein CD44.

Osteopontin is associated with, and plays a role in, the regulation and progression of many diseases. Osteopontin is known to be increased in a number of autoimmune disorders and is overexpressed in a variety of cancers. Plasma levels of osteopontin are also elevated in individuals with coronary artery disease and elevated levels of osteopontin are found in the synovial fluid of individuals with rheumatoid arthritis.

Modulation of osteopontin may, therefore, confer significant therapeutic benefits. Accordingly, there is a need to identify means to regulate osteopontin, especially means to lower the effective osteopontin level or concentration.

The present invention is based, at least in part, on the discovery that osteopontin can be regulated by regulating S-adenosyl methionine decarboxylase (AMD1), polyamine biosynthesis, adenosine or a pathway containing either AMD1 or adenosine. Accordingly, the present invention provides methods for the regulation of osteopontin activity in a subject as well as for treating or preventing conditions associated with an increased activity of osteopontin activity in a subject.

The present invention provides a method of decreasing the activity of osteopontin in a cell. The method comprises contacting a cell with an effective amount of an agent that inhibits S-adenosyl methionine decarboxylase ("AMD1"), inhibits polyamine biosynthesis, or increases adenosine in the cell.

According to another aspect, the present invention provides a method of decreasing the activity of osteopontin in a cell by contacting the cell with an effective amount of MGBG, a salt of MGBG, or a protected derivative of MGBG.

According to another aspect, the present invention provides a method of treating or preventing a condition associated with an increased activity of osteopontin. The method comprises administering to a subject in need of such treatment an effective amount of an agent that inhibits S-adenosyl methionine decarboxylase, inhibits polyamine biosynthesis, or increases adenosine in the subject, with the proviso that the agent is not MGBG, a polyamine analog or a salt or protected derivative thereof.

According to yet another aspect, the present invention provides a method of treating a condition. The method comprises administering to a subject in need of such treatment an effective amount of MGBG, a salt of MGBG, a protected derivative of MGBG, or a polyamine analog, a salt, a protected derivative, or a stereoisomer thereof, wherein the condition is selected from the group consisting of Crohn's disease, Parkinson's disease, inflammatory bowel disorder, multiple sclerosis (MS), amyotrophic lateral sclerosis (ALS), hepatitis, HBV, HCV, nephritis, cerebritis, glomerulonephritis, rheumatoid arthritis, type 2 diabetes, cardiac fibrosis and angiotensin type II associated hypertension, osteoporosis, a mast cell produced IgE mediated hypersensitivity immune reaction, peripheral sensory neuropathy associated with HIV infection or diabetes mellitus, asthma, autism, dermatomyositis, frailty, obesity, primary biliary cirrhosis, primary sclerosing cholangitis, post-radiation syndrome, psoriatic arthritis, sarcoidosis, scleroderma with or without pulmonary fibrosis, a kidney related autoimmune condition, diabetic nephropathy, a diabetic vascular complication, and a lymphoproliferation related autoimmune condition.

According to yet another aspect, the present invention provides a method of decreasing osteopontin secretion from monocytes or macrophages. The method comprises contacting a monocyte or macrophage with an effective amount of an agent that inhibits S-adenosyl methionine decarboxylase, inhibits polyamine biosynthesis, or increases adenosine in the monocyte or macrophage.

According to yet another aspect, the present invention provides a method of decreasing osteopontin secretion from monocytes or macrophages. The method comprises contacting a monocyte or macrophage with an effective amount of an agent that inhibits S-adenosyl methionine decarboxylase, inhibits polyamine biosynthesis, or increases adenosine in the monocyte or macrophage.

According to yet another aspect, the present invention provides a method of decreasing differentiation of macrophages from monocytes. The method comprises contacting a monocyte with an effective amount of an agent that inhibits S-adenosyl methionine decarboxylase, inhibits polyamine biosynthesis, or increases adenosine in the monocyte.

These and other features of the present invention are set forth below.

BRIEF DESCRIPTION OF THE DRAWINGS

The skilled artisan will understand that the drawings are for illustration purposes only. The drawings are not intended to limit the scope of the present invention in any way.

Figure 1:
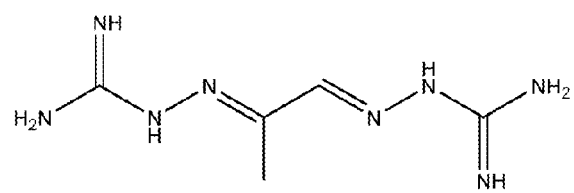
FIG. 1 shows the structures of MGBG, SL47 (also referred to as SL11047) and SL 93 (also referred to as SL11093).
Figure 1:
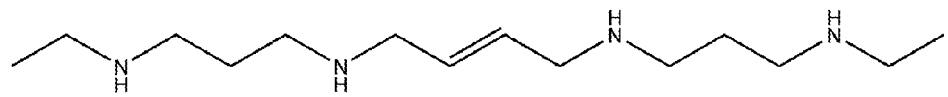
Figure 1:
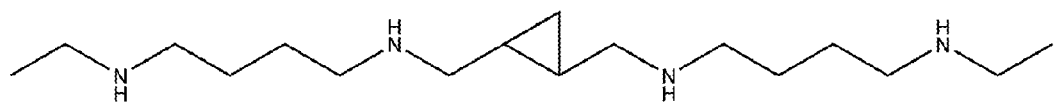
Figure 2A:
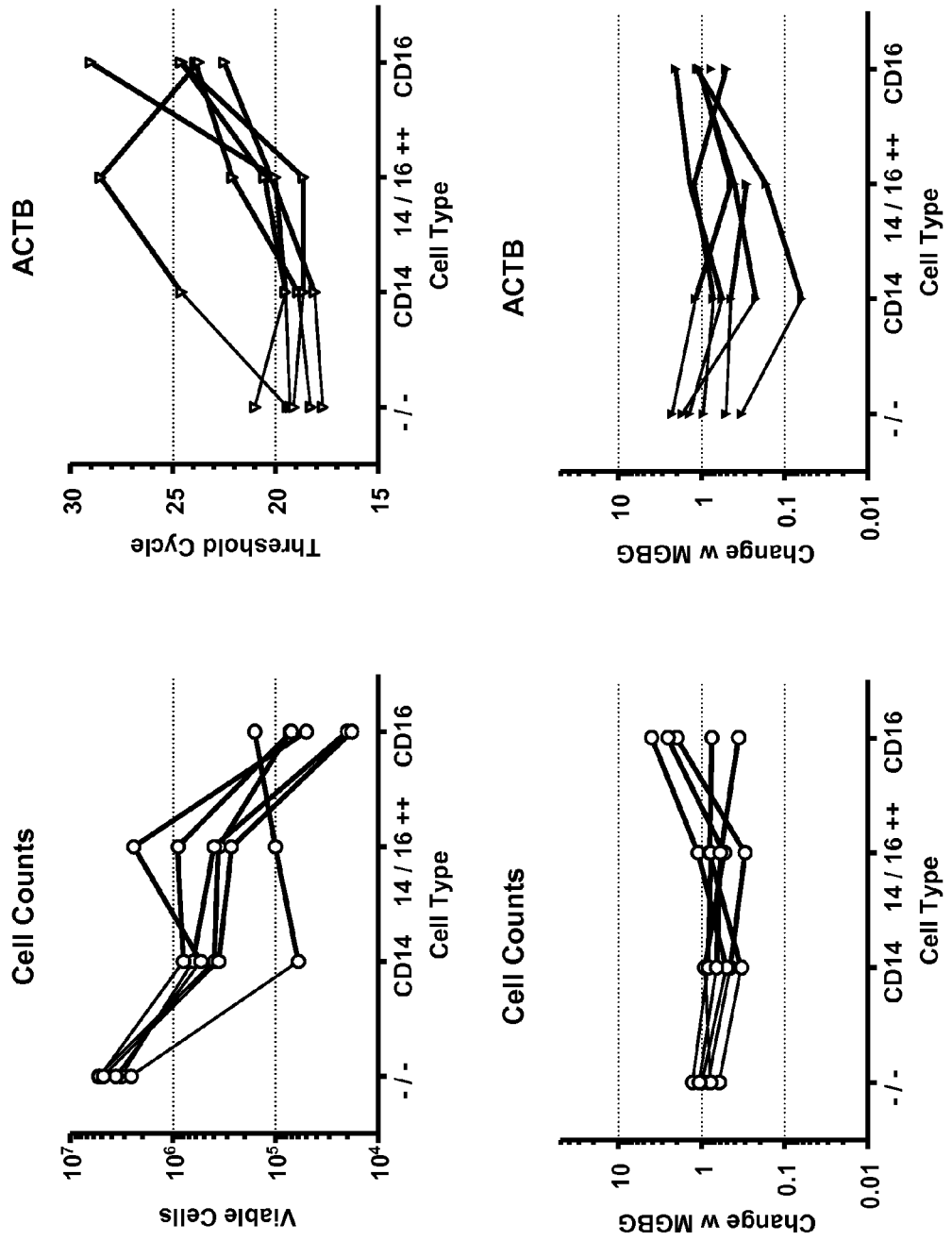
FIGS. 2A-2D depict the changes in cell counts and RNA signals of OPN, ADA and other genes induced by MGBG in mononuclear cells separated on the basis of cell-surface CD14 and CD16 expression.
Figure 2B:
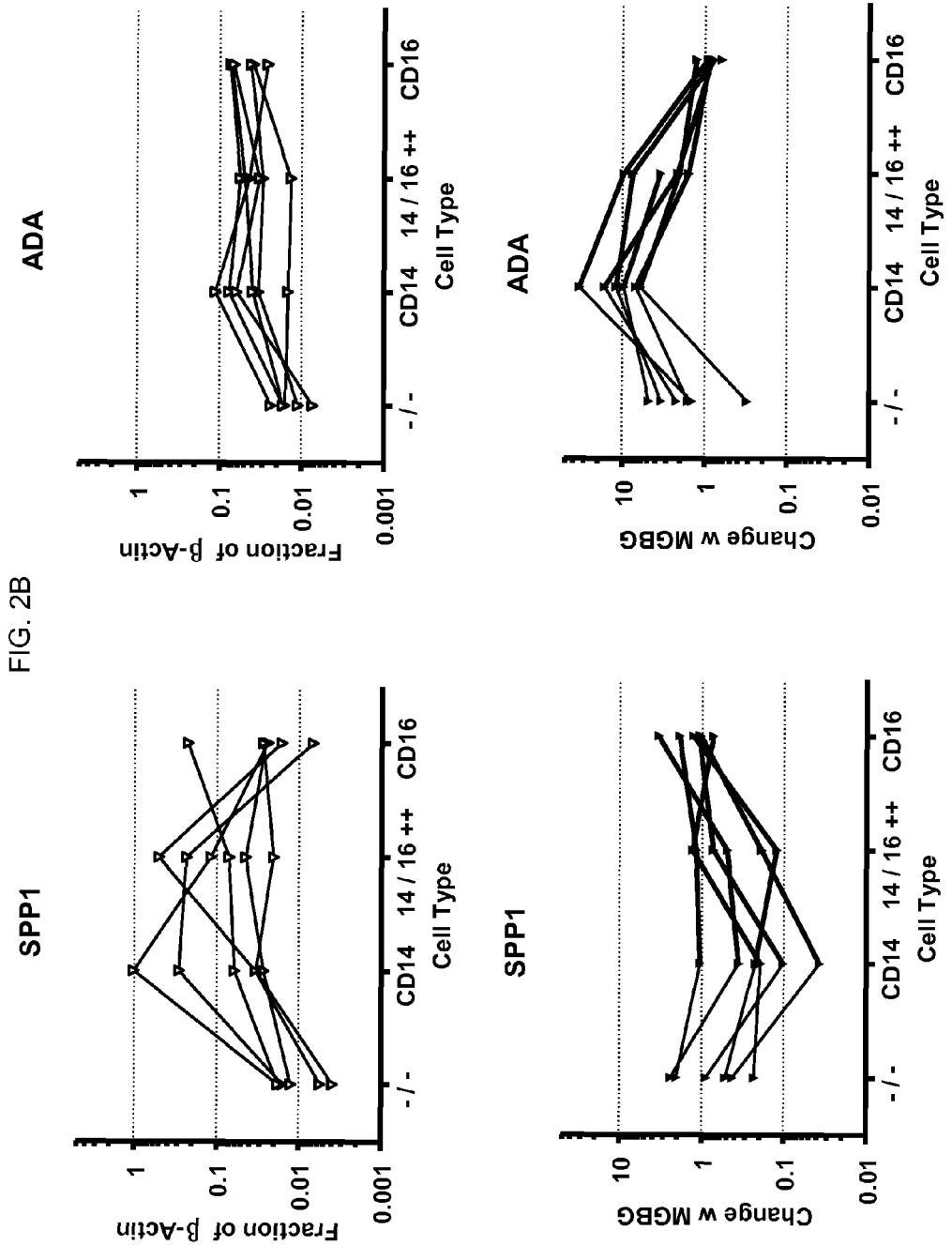
Figure 2C:
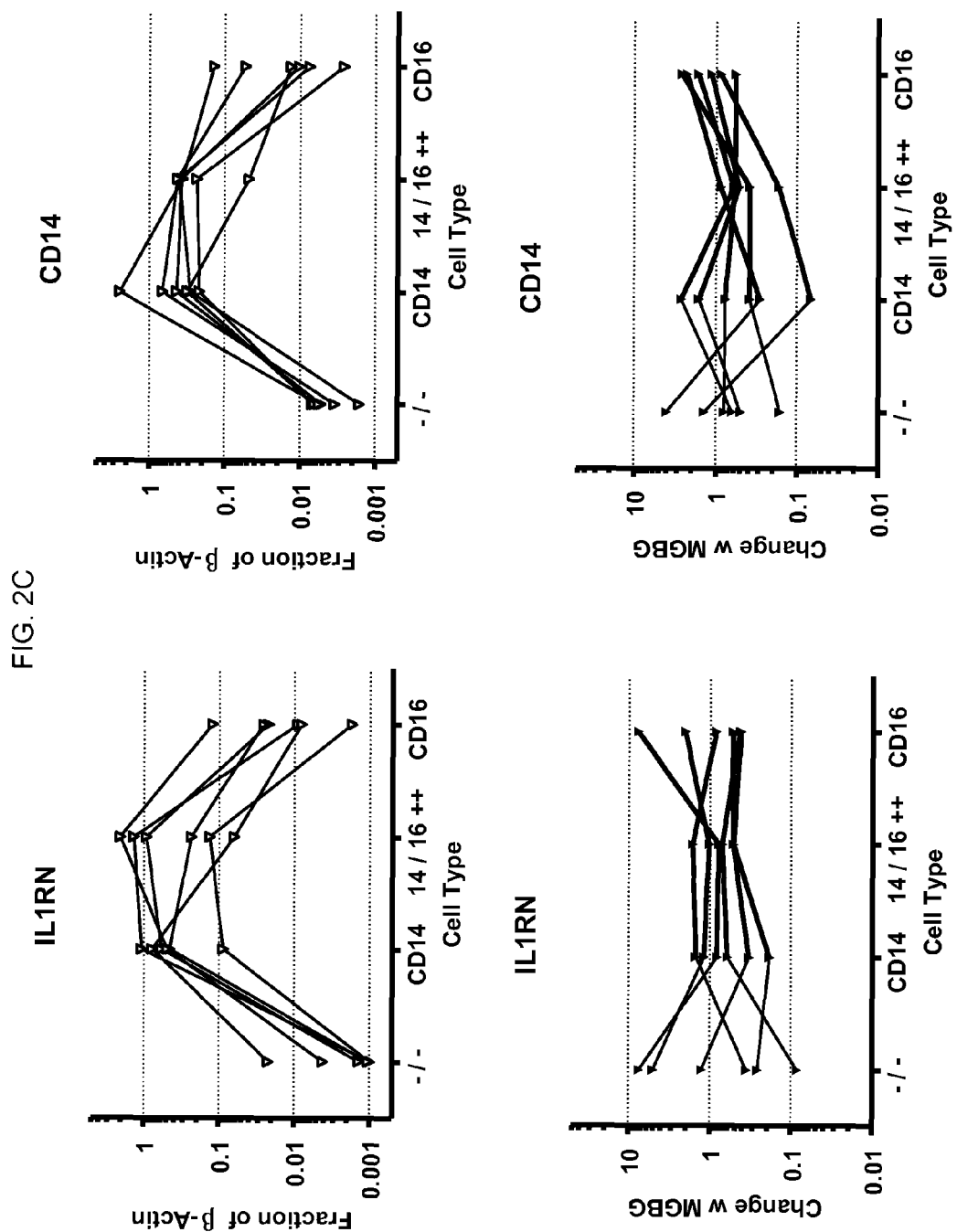
Figure 2D:
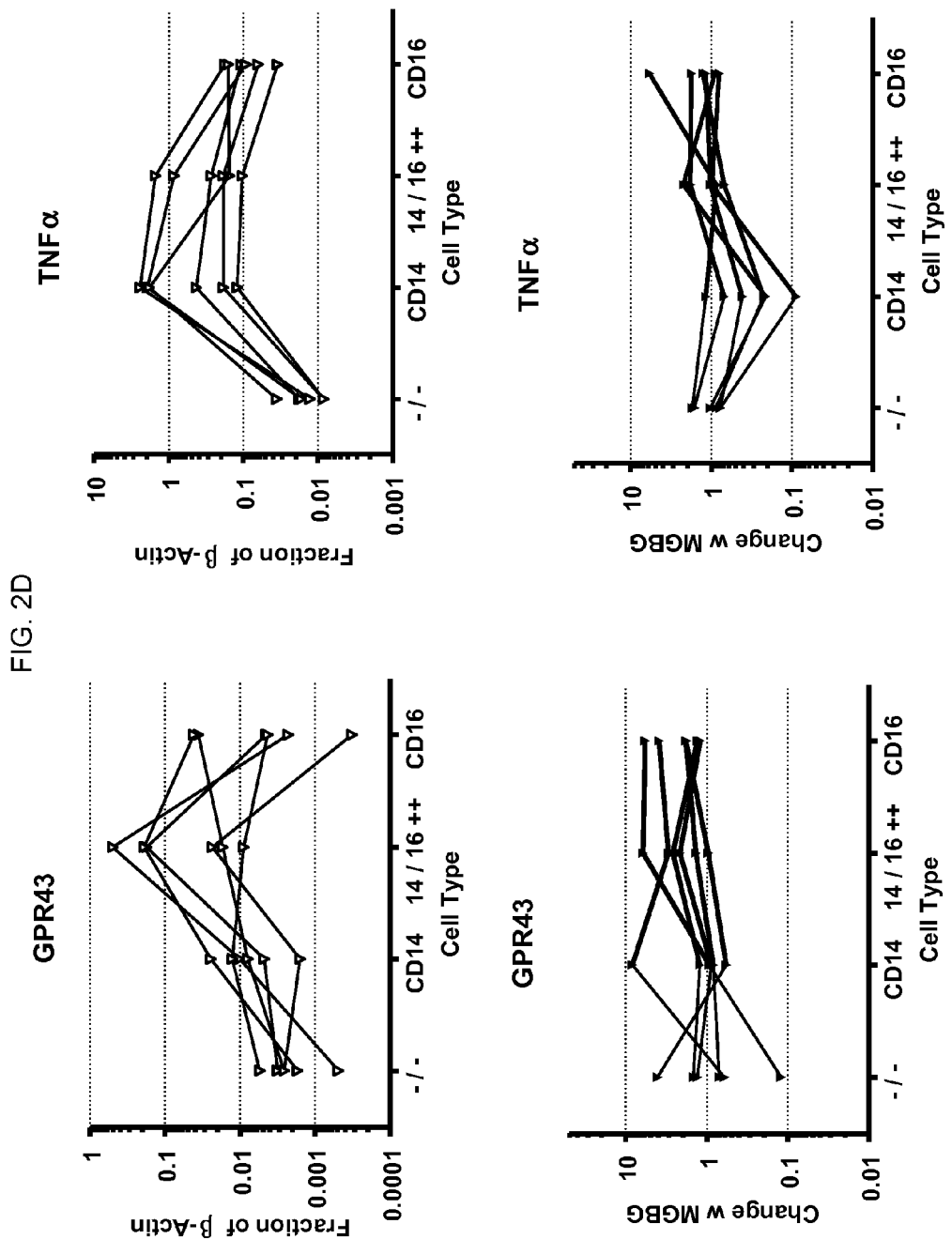

The present invention is based, at least in part, on the discovery that osteopontin can be regulated by regulating S-adenosyl methionine decarboxylase ("AMD1"), polyamine biosynthesis, adenosine or a pathway containing either AMD1 or adenosine. Accordingly, the present invention provides methods for the regulation of osteopontin activity in a subject as well as for treating or preventing conditions associated with an increased activity of osteopontin activity in a subject.

According to one aspect, the present invention provides a method of decreasing the activity of osteopontin in a cell. The term "osteopontin" is used interchangeably with "OPN," "SPP1," "Eta-1," sialoprotein 1 or 44K BPP (bone phosphoprotein). In general, osteopontin refers to any full-length or partial fragment of a full-length osteopontin. Osteopontin can also refer to any modified, e.g., glycosylated, osteopontin.

The term "activity" as used herein refers to both, the biological activity of the polypeptide and to the quantity or level of osteopontin present in the cell. In one embodiment, the term activity refers to the quantity of osteopontin, e.g., present, expressed or produced in the cell. In another embodiment, it refers to the level of osteopontin secreted by the cell, for example, by a mononuclear cell.

According to another aspect, the present invention provides a method of treating or preventing a condition associated with an increased activity of osteopontin. The method comprises administering to a subject in need of such treatment an effective amount of an agent that regulates the activity of osteopontin. The condition can be any condition now known, or later discovered, to be associated with an increased activity of osteopontin. Examples of conditions associated with an increased activity of osteopontin include, but are not limited to, autoimmune diseases, inflammatory diseases, neoplastic growth and tumor metastases. In one embodiment, the condition associated with an increased activity of osteopontin is infiltration of immune cells to an affected area or increased level of CD14/CD16 macrophages in a subject.

In another embodiment, conditions associated with an increased activity of osteopontin include, but are not limited to, multiple sclerosis (MS), atherosclerosis and related coronary diseases, rheumatoid arthritis, lupus, nephritis, cerebritis, Crohn's disease, osteoporosis, inflammatory bowel disorder, breast cancer, ovarian cancer, pancreatic cancer, bladder cancer, lung cancer, colon cancer, gastric carcinomas, esophageal carcinomas, squamous cell carcinomas of the head or neck, prostate cancer, thyroid cancer, melanoma, kidney cancers, renal cell carcinomas, endometrial cancer, small intestine cancer, duodenal cancer, cholangiocarcinoma, astrocytoma, AIDS lymphoma, follicular lymphoma, T-cell lymphoma, B-cell lymphoma, proliferative retinopathy, vitreoretinopathy, diabetic retinopathy, macular degeneration, non-HIV dementia, HIV- and AIDS-associated dementia, focal segmental glomerulosclerosis, membrane proliferative glomerulonephropathy, psoriasis, herpes virus associated disease, Castleman's disease, Kaposi's sarcoma, Alzheimer's disease, type 2 diabetes, cardiac fibrosis and angiotensin type II associated hypertension, mast cell produced IgE mediated hypersensitivity immune reactions, prelymphomatic or lymphoproliferation related autoimmune conditions, angioimmunoblastic lymphadenophathy (AILD), glomerulonephritis and other glomerular diseases, immunoglobulin A (IgA) nephropathy, Amyotrophic Lateral Sclerosis (ALS), hepatitis including HBV and HCV, peripheral sensory neuropathy associated with HIV infection or diabetes mellitus, asthma, autism, dermatomyositis, frailty, obesity, Parkinson's disease, primary biliary cirrhosis, primary sclerosing cholangitis, post-radiation syndrome, psoriatic arthritis, sarcoidosis, scleroderma with or without pulmonary fibrosis, kidney related autoimmune conditions, diabetic nephropathy and other diabetic vascular complications.

In yet another embodiment, the condition associated with an increased activity of osteopontin is not associated with macrophage proliferation.

A "subject" may be any animal suffering from a condition associated with an increased activity of osteopontin that is treatable in accordance with the methods of the invention. An animal is a living multicellular vertebrate organism, and includes both human and non-human mammals.

An "effective amount" or a "therapeutically effective amount" is a quantity of a compound (e.g., MGBG, a polyamine analog or any agent) that is sufficient to achieve a desired effect in a subject being treated. For instance, this can be the amount necessary to reduce osteopontin activity or to otherwise measurably alter or alleviate the symptoms of increased osteopontin activity. The effective amount of a compound of the present invention may vary depending upon the route of administration and dosage form. In addition, specific dosages may be adjusted depending on conditions of disease, the age, body weight, general health conditions, sex, and diet of the subject, dose intervals, administration routes, excretion rate, and combinations of agents.

According to yet another aspect, the present invention provides a method of decreasing osteopontin secretion from monocytes or macrophages. The method comprises contacting a monocyte or macrophage with an effective amount of an agent that regulates the activity of osteopontin.

According to yet another aspect, the present invention provides a method of decreasing differentiation of macrophages from monocytes. The method comprises contacting a monocyte with an effective amount of an agent that regulates the activity of osteopontin.

The agent useful in the methods of the invention can be any agent that decreases the activity of osteopontin. In one embodiment, the agent is capable of inhibiting S-adenosyl methionine decarboxylase ("AMD1") or any pathway containing AMD1, e.g., any entity upstream or downstream of a pathway containing AMD1, especially any pathway containing AMD1 and associated with adenosine production. In another embodiment the agent is capable of inhibiting polyamine biosynthesis or any pathway involved in polyamine biosynthesis.

Alternatively the agent is capable of increasing the activity of adenosine in the cell, either directly, or via a pathway containing adenosine. In general, a pathway containing AMD1 or adenosine is understood to refer to a pathway in which either AMD1 or adenosine is involved, including, for example, as a substrate, catalyst, product or by-product.

The agent can be any kind of known or later discovered agent that can inhibit the activity of the enzyme S-adenosyl methionine decarboxylase, can inhibit polyamine biosynthesis, or that can increase the activity of adenosine in, for example, a cell. In one embodiment, the agent is a chemical agent, including, but not limited to, organic molecules and salts, protected derivatives and stereoisomers thereof, inorganic molecules or various ionic or elemental entities. In another embodiment, the agent is a biological agent or a biomolecule, for example, a polypeptide, an antibody or an active fragment thereof, or a nucleic acid molecule, e.g., RNAi.

According to one embodiment of the present invention, the agent is a polyamine analog or a salt, a protected derivative, or a stereoisomer thereof. Any polyamine analog is suitable for use in the methods of the present invention. Exemplary polyamine analogs used in the methods of the invention include compounds of the structures 1, 2, 3, 4, and 5, and the corresponding stereoisomers, salts, and protected derivatives thereof:

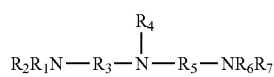

1 where $R_1$, $R_2$, $R_4$, $R_6$ and $R_7$ are independently selected from the group consisting of hydrogen, alkyl and aryl, and where $R_3$ and $R_5$ are alkyl groups;

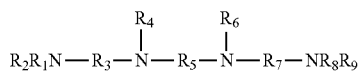

2 where R1, R2, R4, R6, R8, and R9 are independently selected from the group consisting of hydrogen, alkyl and aryl and where R3, R5 and R7 are alkyl groups;

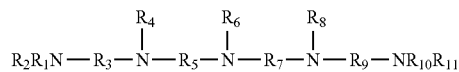

3 where $R_1$, $R_2$, $R_4$, $R_6$, $R_{10}$ and $R_{11}$ are independently selected from the group consisting of hydrogen, alkyl and aryl, and where $R_3$, $R_5$, $R_7$ and $R_9$ are alkyl groups;

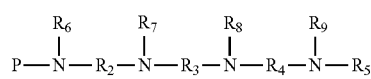

4 where $R_1$ and $R_5$ are independently selected from the group consisting of methyl, ethyl, n-propyl, and isopropyl;
where $R_2$, $R_3$, and $R_4$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl;
and where $R_6$, $R_7$, $R_8$ and $R_9$ are independently selected from the group consisting of H, methyl, and ethyl;

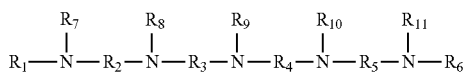

5 where $R_1$ and $R_6$ are independently selected from the group consisting of methyl, ethyl, n-propyl, and isopropyl;
$R_2$, $R_3$, $R_4$ and $R_5$ are independently selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ aryl-$C_1$-$C_6$ alkyl;
and where $R_7$, $R_8$, $R_9$, $R_{10}$ and $R_{11}$ are independently selected from the group consisting of H, methyl, and ethyl.

In another embodiment, the polyamine analogs are compounds of the structures 2 and 3, where $R_3$, $R_5$, $R_7$ and $R_9$ are independently $(CH_2)_x$ groups, where x is an integer from 2 to 6, and further where $R_4$, $R_6$ and $R_8$ are hydrogen atoms.

In yet another embodiment, the polyamine analogs are compounds of the structures 2 and 3, where $R_3$, $R_5$, $R_7$ and $R_9$ are independently $(CH_2)_2$ groups, where x is an integer from 2 to 6, and where $R_4$, $R_6$ and $R_8$ are hydrogen atoms, and where $R_1$ and $R_{10}$ are alkyl groups, and further where $R_2$ and $R_{11}$ are hydrogen atoms.

In yet another embodiment, the polyamine analogs are compounds of the structures 2 and 3, where $R_3$, $R_5$, $R_7$ and $R_9$ are independently $(CH_2)_2$ groups, where x is an integer from 2 to 6, and where $R_4$, $R_6$ and $R_8$ are hydrogen atoms, and where $R_1$ and $R_{10}$ are alkyl groups, and where $R_2$ and $R_{11}$ are hydrogen atoms, and further where the polyamine analogs have a molecular weight less than 500.

Further embodiments of compounds of the structure 4 include those where $R_6$, $R_7$, $R_8$ and $R_9$ are H;
where $R_1$ and $R_5$ are ethyl;
where $R_6$, $R_7$, $R_8$ and $R_9$ are H and $R_1$ and $R_5$ are ethyl;
and/or where $R_2$ and $R_4$ are independently selected from the group consisting of $C_1$-$C_6$ alkyl and
$R_3$ is selected from the group consisting of $C_1$-$C_6$ alkyl, $C_2$-$C_6$ alkenyl, $C_3$-$C_6$ cycloalkyl, $C_1$-$C_6$ alkyl-$C_3$-$C_6$ cycloalkyl-$C_1$-$C_6$ alkyl, $C_3$-$C_{10}$ aryl, and $C_1$-$C_6$ alkyl-$C_3$-$C_{10}$ aryl-$C_1$-$C_6$ alkyl.

Additional polyamine analogs useful in the present invention include compounds of the formula 6, and the corresponding stereoisomers, salts, and protected derivatives thereof:

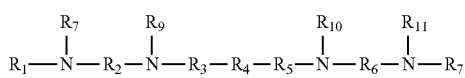

6 where $R_4$ is $C_2$-$C_6$ n-alkenyl, $C_3$-$C_6$ cycloalkyl, $C_3$-$C_6$ cycloalkenyl, or $C_3$-$C_6$ aryl;
$R_3$ and $R_5$ are independently chosen from a single bond, $C_1$-$C_6$ alkyl, or $C_1$-$C_6$ alkenyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are H.

In certain embodiments of the compounds of formula 6, $R_1$ and $R_7$ are independently chosen from $C_1$-$C_6$ alkyl or $C_2$-$C_6$ alkenyl.

Additional polyamine analogs useful in the present invention include compounds of the formula 7, and the corresponding stereoisomers, salts, and protected derivatives thereof:

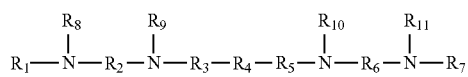

7 where $R_4$ is $C_1$-$C_6$ n-alkyl or $C_1$-$C_6$ branched alkyl;

$R_3$ and $R_5$ are independently chosen from a single bond or $C_1$-$C_6$ alkyl;

$R_2$ and $R_6$ are independently chosen from $C_1$-$C_6$ alkyl, $C_1$-$C_6$ alkenyl, $C_3$-$C_6$ cycloalkyl, $C_3$-$C_6$ cycloalkenyl, or $C_3$-$C_6$ aryl;

$R_1$ and $R_7$ are independently chosen from H, $C_1$-$C_6$ alkyl, or $C_2$-$C_6$ alkenyl; and $R_8$, $R_9$, $R_{10}$, and $R_{11}$ are H.

In certain embodiments of the compounds of formula 7, $R_2$ and $R_7$ are independently chosen from $C_1$-$C_6$ alkyl or $C_2$-$C_6$ alkenyl, $R_4$ is $C_1$-$C_6$ saturated n-alkyl or $C_1$-$C_6$ saturated branched alkyl, and $R_3$ and $R_5$ are independently chosen from a single bond or $C_1$-$C_6$ saturated n-alkyl.

As used herein, a "polyamine" is any of a group of aliphatic, straight-chain amines derived biosynthetically from amino acids; polyamines are reviewed in Marton et al. (1995) Ann. Rev. Pharm. Toxicol. 35:55-91. By "polyamine" is generally meant a naturally-occurring polyamine or a polyamine which is naturally produced in eukaryotic cells. Examples of polyamines include putrescine, spermidine, spermine and cadaverine.

As used herein, a "polyamine analog" is an organic cation structurally similar but non-identical to naturally-occurring polyamines such as spermine and/or spermidine and their precursor, diamine putrescine. Polyamine analogs can be branched or un-branched, or incorporate cyclic moieties. Polyamines may comprise primary, secondary, tertiary, or quaternary amino groups. In one embodiment, all the nitrogen atoms of the polyamine analogs are independently secondary, tertiary, or quaternary amino groups, but are not so limited. Polyamine analogs may include imine, amidine and guanidine groups in place of amine groups. The term "polyamine analog" includes stereoisomers, salts and protected derivatives of polyamine analogs.

A "stereoisomer" is any optical isomer of a compound, including enantiomers and diastereomers. Unless otherwise indicated, structural formulae of compounds are intended to embrace all possible stereoisomers.

A "salt" or "pharmaceutically acceptable salt" is a compound formed by the replacement of one or more hydrogen atoms with elements or groups, which is composed of anions and cations, which usually ionizes in water; a salt is formed, for instance, by neutralization of an acid by a base. Examples of salts include, but are not limited to, halide, for example, chloride, bromide, or iodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

"Protected derivative" is used to refer to a compound protected with a protecting group. "Protecting group" refers to a chemical group that exhibits the following characteristics: 1) reacts selectively with the desired functionality in good yield (preferably at least 80%, more preferably at least 90%, more preferably at least 95%, still more preferably at least 99%) to give a protected substrate that is stable to the projected reactions for which protection is desired; 2) is selectively removable from the protected substrate to yield the desired functionality; and 3) is removable in good yield (preferably at least 80%, more preferably at least 90%, more preferably at least 95%, still more preferably at least 99%) by reagents compatible with the other functional group(s) present or generated in such projected reactions. Examples of suitable protecting groups can be found in Greene et al. (1991) Protective Groups in Organic Synthesis, 2nd Ed. (John Wiley & Sons, Inc., New York). Exemplary protecting groups for the amino functionality include, but are not limited to, mesitylenesulfonyl (MesSO$_2$), benzyloxycarbonyl (CBz), t-butyloxycarbonyl (Boc), t-butyldimethylsilyl (TBDIMS), 9-fluorenylmethyloxycarbonyl (Fmoc), or suitable photolabile protecting groups such as 6-nitroveratryloxy carbonyl (Nvoc).

An "alkyl" is a cyclic, branched, or straight chain chemical group containing carbon and hydrogen, such as methyl, butyl, t-butyl, pentyl, cyclopropyl, and octyl. Alkyl groups can be either unsubstituted or substituted with one or more substituents, e.g., halogen, alkoxy, acyloxy, amino, hydroxyl, mercapto, carboxy, benzyl. Alkyl groups can be saturated or unsaturated (e.g., containing —C═C— or —C≡C— subunits), at one or several positions. Unless otherwise specified, alkyl groups will comprise 1 to 8 carbon atoms, but may include 1 to 6, or even 1 to 4 carbon atoms. "Cycloalkyl" refers to cyclic alkyl groups only, such as cyclopropyl, cyclobutyl, cyclopentyl, etc. "n-alkyl" refers to a linear (i.e., straight-chain) alkyl group only, while "branched alkyl" refers to branched alkyl groups to the exclusion of cyclic and linear alkyl groups. "Alkenyl" refers to a cyclic, branched, or straight chain chemical group containing carbon and hydrogen where at least one bond is monounsaturated, such as ethenyl, cyclopentenyl, or 1,3-butadienyl. Alkenyl groups can be substituted as indicated for alkyl groups. Alkenyl groups can be designated as cyclic, linear (n-alkenyl) or branched in an analogous fashion to the preceding designations for alkyl. An "aryl" is an unsaturated aromatic carbocyclic group having a single ring (e.g., phenyl), or multiple condensed rings (e.g., naphthyl), which can optionally be unsubstituted or substituted with amino, hydroxyl, alkyl, alkoxy, chloro, halo, mercapto and other substituents.

According to another embodiment of the present invention, the agent is a chemical moiety that inhibits the activity of S-adenosyl methionine decarboxylase, inhibits polyamine biosynthesis, and/or increases the activity of adenosine. Examples of such moieties include, but are not limited to, those listed in Table 1. Irrespective of the form of the moiety listed in Table 1, it is understood that it includes, as applicable, a salt, protected derivative, and stereoisomer thereof.

TABLE 1

Exemplary Inhibitors of S-adenosyl methionine decarboxylase and/or polyamine biosynthesis

| Compound | Official Name (Not IUPAC) | Pub Chem ID |
|---|---|---|
| Decarboxylated SAM | s-adenosyl-3-methylthiopropylamine | |
| Mitoguazone or "MGBG" | Methylglyoxal bis(guanyl-hydrazone) | 5351154 |
| EGBG | Ethylglyoxal bis(guanylhydrazone) | 9561662 |
| Berenil | Diminazene or Diminazene aceturate | 2354 |
| Pentamidine | 4-[5-(4-carbamimidoylphenoxy)pentoxy]benzenecarboximidamide | 4735 |
| | 5'-(Dimethylsulphino)-5'-deoxyadenosine | |
| | S-adneosyl-4-methylthiobutyrate | |
| | S-adenosyl-S-methyl-L-cysteine | |
| AMA | S-(5'-Deoxy-5'-adenosyl) methylthioethylhydroxylamine | |
| EMGBG | Ethylmethylglyoxal bis(guanylhydrazone) | 9574151 |
| DEGBG | Diethylglyoxal bis(guanylhydrazone) | 5479208 |
| CGP-33'829 | 6-((2-carbamimidoylhydrazono)methyl)picolinimidamide | |
| CGP-36'958 | | |
| CGP-39'937 | 2,2'-bipyridine-6,6'-bis(carboximidamide) | |
| CGP-48664 or CGP-48664A or SAM 364A | 4-amidinoindan-1-one 2'-amidinohydrazone | 5486811 |
| AbeAdo or MDL-73811 | 5'-[[(Z)-4-amino-2-butenyl] methylamino]-5'-deoxyadenosine | 6436013 |
| MAOEA | 5'-deoxy-5'-[N-methyl-N-[2-(aminooxy)ethyl]amino]adenosine | 3081018 |
| MHZPA | 5'-deoxy-5'-[N-methyl-N-(3-hydrazinopropyl)amino]adenosine | 122092 |
| MHZEA | 5'-deoxy-5'-[(2-hydrazinoethyl)-methylamino]adenosine | |
| AdoMac | S-(5'-deoxy-5'-adenosyl)-1-ammonio-4-(methylsulfonio)-2-cyclopentene | 3083364 |
| AdoMao | S-(5'-deoxy-5'-adenosyl)-1-aminoxy-4-(methylsulfonio)-2-cyclopentene | |
| APA | 1-Aminooxy-3-aminopropane | 65020 |
| AOE-PU | N-[2-aminooxyethyl]-1,4-diaminobutane | |
| AP-APA | 1-aminooxy-3-N-[3-aminopropyl]-aminopropane | |
| | 1,11-bis(ethyl)norspermine | |
| BES | 1,8-bis(ethyl)spermidine | |
| BES | 1,12-bis(ethyl)spermine | |
| DESPM | N1,N12-diethylspermine | |
| BE-3-3-3 | 1,11-bis(ethylamino)-4,8-diazaundecan | |
| BE-4-4-4 | 1,14-bis(ethylamino)-5,10-diazatetradecane | |
| DEHOP or DEHSPM | Diethylhomospermine, N1,N14-diethylhomospermine | |
| DENOP | diethyl-norspermine | |
| BE-4-4-4-4 | 1,19-bis(ethylamino)-5,10,15-triaza-nonadecane | |
| SL11037 | N-ethyl-N'-(2-(3'-ethylamino-propylamino methyl)-cis-cyclopropylmethyl)-propane 1,3-diamine tetrahydrochloride | |
| SL11038 | N-ethyl-N'-(2-(3'-ethylamino-propylamino methyl)-trans-cyclobutylmethyl)-propane 1,3-diamine tetrahydrochloride | |
| SL11044 | N-ethyl-N'-(2-(3'-ethylamino-propylamino methyl)-trans-cyclopropylmethyl)-propane 1,3-diamine tetrahydrochloride | |
| SL11047 or SL47 | N,N'-bis(3-ethylaminopropyl)-cis-but-2-ene-1,4-diamine tetrahydrochloride | |
| SL11093 or SL93 | N,N'-(cyclopropane-1,2-diylbis(methylene))bis(N4-ethylbutane-1,4-diamine) | |

In yet another embodiment, the agent is a compound selected from the group consisting of MGBG, MDL73811, CGP48664, Berenil, Pentamidine, SL47, and SL93, or a combination of two or more thereof. In yet another embodiment, the agent is MGBG, SL47 or SL93. Structures for MGBG, SL47 and SL93 are shown in FIG. 1. In still another embodiment, two or more agents are used in the methods of the invention to regulate the activity of osteopontin. The two or more agents can be used either sequentially or simultaneously.

In one embodiment, the agent is a compound selected from the list of agents listed in Table 1, with the proviso that the agent is not MGBG. In another embodiment, the agent is not a polyamine analog. In yet another embodiment, the agent is not MGBG or a polyamine analog. In yet another embodiment, the agent is not a polyamine biosynthesis inhibitor. In yet another embodiment, the agent is a compound selected from the group consisting of MDL73811, CGP48664, Berenil and Pentamidine.

"MGBG" is 1,1' [methylethanediylidene]dinitrilodiguanidine and is also known as methylglyoxal bis(guanylhydrazone), methyl-GAG, and mitoguazone. As used herein, MGBG includes the free base and salts thereof. It is commonly, but not necessarily, used as a dihydrochloride.

The agent may also be administered in combination with one or more entities. In one embodiment, the entity is a therapeutic entity, including, but not limited to, a steroid or other anti-inflammatory agent. In another embodiment, the entity is a pharmaceutically acceptable carrier.

The effective amount of an agent that inhibits S-adenosyl methionine decarboxylase or increases the activity of adenosine, e.g., in a cell or a subject, can be any amount that is sufficient to decrease the activity of osteopontin, e.g., in the cell or the subject, typically by about 25%, 30%, 40%, 50%, 60%, 70%, 75%, 80%, 85%, 90%, 95% or more. In one embodiment, the effective amount of an agent is an amount that is sufficient to decrease the activity of osteopontin by 70% or more. In another embodiment, the effective amount of an agent is an amount that is sufficient to decrease the activity of osteopontin by 80% or more. In yet another embodiment, the agent inhibits S-adenosyl methionine decarboxylase and the effective amount is an amount sufficient to activate adenosine deaminase ("ADA"). In still another embodiment, the agent inhibits S-adenosyl methionine decarboxylase and the effective amount is an amount sufficient to increase the activity of adenosine.

The optimal dose, frequency of administration, and duration of treatment with the agent that decreases the activity of osteopontin in a subject may vary from subject to subject, depending on the subject's condition, the subject's age, weight, response to the treatment, and the nature of the therapeutic entity. The optimal dose and duration of treatment may be best determined by monitoring the subject's response during the course of the treatment. In some instances, the administration of higher doses may permit less frequent administration, and lower doses may require more frequent administration in order to achieve a clinically significant improvement in the subject's condition. The agent may be administered as a single dose or in multiple doses.

Generally, a therapeutically effective dose of the agent in accordance with the present methods will be one or more doses of from about 10 to about 1100 mg/m$^2$. Lower dose regiments include doses of 10-200, 10-100, 10-50 and 20-200 mg/m$^2$. Higher dose regimens include 200-400, 250-500, 400-600, 500-800 600-1000 and 800-1100 mg/m$^2$. In one embodiment, the dose regimens range from 200-400 mg/m$^2$. In another embodiment, the dose regimens range from 250-500 mg/m$^2$. In yet another embodiment, the dose regimens range from 600-1000 mg/m$^2$. In some embodiments the agent is administered daily, once per week, once every other week, or once per month. In one embodiment, a dose regimen ranging from 200-400 mg/m$^2$ is administered once a week. In another embodiment, a dose regimen ranging from 250-500 mg/m$^2$ is administered once every other week.

The doses may be constant over the entire treatment period, or they may increase or decrease during the course of the treatment. In one embodiment, the agent is administered once a week and starts with the administration of 200 mg/m$^2$ and increases to 300 mg/m$^2$ and 400 mg/m$^2$ in the second and third weeks, respectively. In another embodiment, the agent is administered once every other week and is kept constant for the entire duration of treatment with the administration of 250 mg/m$^2$. The doses of the agent may be administered for at least one week, at least two weeks, at least three weeks, at least four weeks, at least 6 weeks, or even at least 8 weeks. Adjusting the dose of the agent within these ranges for a particular subject is well within the skill of the ordinary clinician.

The agent may be administered via any conventional route normally used to administer a medicament including, but not limited to, intravenous routes, parenteral routes (e.g., intradermal, intramuscular or subcutaneous routes), oral routes and nasal routes. The agent may be administered as a pharmaceutical composition in a variety of forms including, but not limited to, liquid, powder, suspensions, tablets, pills, capsules, sprays and aerosols. The pharmaceutical compositions may include various pharmaceutically acceptable additives including, but not limited to, carriers, excipients, binders, stabilizers, antimicrobial agents, antioxidants, diluents and/or supports. Examples of suitable excipients and carriers are described, for example, in "Remington's Pharmaceutical Sciences," Mack Pub. Co., New Jersey (1991). In some embodiments, the agent may be administered via an IV infusion in an aqueous sugar solution. The agent may also be associated with another substance that facilitates agent delivery. For example, the agent may be associated into liposomes. The liposomes, in turn, may be conjugated with targeting substance(s), such as IgGFc receptors.

Exemplary embodiments of the present methods are provided in the following examples. The following examples are presented to illustrate the methods of the invention and to assist one of ordinary skill in using the same. The examples are not intended in any way to otherwise limit the scope of the invention.

EXAMPLES

Example 1: Microarray Analysis of Gene Expression Changes Induced by MGBG

Blood samples were obtained from HIV infected patients (N=9) with positive viral load and reduced CD4 counts, and non-HIV infected, healthy controls (N=6). Blood was collected into heparin anticoagulant tubes and mononuclear cells were isolated by Percoll gradient centrifugation. The cells from each sample were split into 2: one-half receives MGBG at concentration of 10 µM and the other half received no treatment. All samples were then cultured overnight in RPMI media with 10% fetal bovine serum at 37° C. under non-adherent conditions. The next day cells were collected by centrifugation, washed one time with PBS, and lysed by resuspension in TRIZOL, and total RNA was prepared according to manufacturer's instructions (Invitrogen, Carlsbad, Calif.). The quality of the RNA was checked by visualizing rRNA bands using a 2100 Bioanalyzer (Agilent Technologies, see Table 2 for ratio of 28 to 18S rRNA). The RNA was then amplified for microarray analysis using a 2 cycle amplification protocol according to the manufacturer's instructions (Affymetrix, Santa Clara, Calif.). The amplified RNAs were then hybridized to Human Genome U133 plus 2.0 microarrays (Affymetrix) and expression data was obtained using an Affymetrix scanner and GCOS protocols. Microarray data was analyzed with GeneSpring Microarray Suite. Results were normalized using a set of 100 probe sets determined by the manufacturer to have relatively invariant expression across most cell types. The clinical parameters of the samples employed, the RNA quality analysis (ratio of 28 to 18S rRNA peaks) and the number of the 54,675 probes called present are presented in Table 2.

TABLE 2

Clinical and RNA sample characteristics

| Sample | Type | % CD14/16 | CD14 HLA-DR | CD4/ µl | Viral Load | % Reduction 14/16 | % Reduction 14 | rRNA − | rRNA + | % Present − | % Present + |
|---|---|---|---|---|---|---|---|---|---|---|---|
| H5-1293 | HIV | 68% | 1390 | | | | | 1.5 | 1.7 | 46.5% | 46.7% |
| H5-1294 | HIV | 62% | 935 | 12 | 46.4 | | | 1.0 | 1.9 | 40.0% | 46.8% |
| H5-1327 | HIV | 35% | 805 | 43 | 712 | <0% | <0% | 1.3 | 1.3 | 42.9% | 45.3% |
| H5-1333 | HIV | 53% | 861 | 567 | 13.6 | 71% | 58% | 1.7 | 1.6 | 46.6% | 47.2% |
| H6-004 | HIV | 55% | 1161 | 567 | 13.6 | 26% | 26% | 0.1 | 0.1 | 41.2% | 43.5% |
| H6-017 | HIV | 38% | 882 | 240 | 31.0 | | 21% | 0.1 | 0.2 | 44.2% | 43.6% |

TABLE 2-continued

Clinical and RNA sample characteristics

| Sample | Type | % CD14/CD16 | CD14 HLA-DR | CD4/ μl | Viral Load | % Reduction 14/16 | % Reduction 14 | rRNA − | rRNA + | % Present − | % Present + |
|---|---|---|---|---|---|---|---|---|---|---|---|
| H6-071 | HIV | 54% | 615 | 11 | >500 | | | 1.5 | 1.4 | 42.5% | 41.4% |
| H6-144 | HIV | 38% | 557 | 54 | 43.0 | 53% | 53% | 1.2 | 1.0 | 40.3% | 37.3% |
| H6-145 | HIV | 18% | 438 | 567 | 13.0 | 91% | 76% | 1.3 | 1.5 | 46.5% | 47.8% |
| Average | | 46.8% | 849 | 258 | 124.7 | 60.3% | 46.8% | 1.1 | 1.2 | 43.4% | 44.4% |
| C6-019 | Healthy | | 469 | | | | | 1.4 | 1.2 | 43.3% | 41.6% |
| C6-139 | Healthy | 41% | 1105 | | | 54% | 26% | 1.8 | 1.8 | 48.0% | 46.6% |
| C6-146 | Healthy | 73% | 1950 | | | 61% | 31% | 1.7 | 1.5 | 47.5% | 48.2% |
| C6-186 | Healthy | 30% | 634 | | | | | 1.8 | 1.8 | 49.6% | 47.9% |
| C6-187 | Healthy | 19% | 667 | | | | | 1.8 | 1.7 | 48.8% | 45.7% |
| M6-177 | ALS | 23% | 496 | | | | | 1.7 | 1.8 | 47.2% | 45.0% |
| Average | | 37.2% | 887 | | | 57.5% | 28.5% | 1.7 | 1.6 | 47.4% | 45.8% |

Blank cells indicate no data was available.
Viral load values are in thousands per milliliter of plasma.
% reduction indicates decrease in yield of CD14+ or CD14/16++ cells in the presence of 10 μM MGBG as determined on the 5th day of culture.
Number of cells in presence and absence of drug was quantitated by flow cytometry.
rRNA indicates the ratio of the 28 to 18S rRNA peak as determined by the 2100 Bioanalyzer from each sample in the in the absence (−) and presence of MGBG (+).
Note 1.8 to 2.0 is considered a perfect ratio.
% Present indicates number of probes called present by GCOS from each sample in the absence (−) and presence of MGBG (+)

Using the average signals obtained from the MGBG and untreated samples, 489 probes are down-regulated at least 1.5 fold and 382 probes are up-regulated at least 1.5 fold. Not all of these probes were consistently changed (e.g. always up regulated or down regulated). For example results obtained with a Probe set specific to TNFα are presented in Table 2. Although the average change in the presence of MGBG for the TNFα Probe set was 8.7 fold up-regulated, inspection of the results of individual samples shows that 2 out of 6 controls and 6 out of 9 HIV infected individuals were less than 2 fold changed in the presence of MGBG relative to incubation without drug (Tables 3A and 3B). Similarly, although the average change in IL10 signal in the presence of MGBG was 5.6 fold upregulated, inspection of the individual samples revealed that increased signals in the presence of MGBG primarily occurred in HIV infected samples but not controls (Tables 4A and 4B).

TABLE 3A

Results obtained with probe for TNFα. Probe ID = 207113_s_at

| | C6-139 | C6-146 | C6-19 | C6-186 | C6-187 | M6-177 |
|---|---|---|---|---|---|---|
| MGBG | 112.4 | 308.3 | 325.3 | 256.8 | 725.4 | 840.6 |
| ON | 104.3 | 150.7 | 185.7 | 110.1 | 147.8 | 146.1 |
| Ratio MGBG/ON | 1.08 | 2.05 | 1.75 | 2.33 | 4.91 | 5.75 | samples not significantly changed in the presence of MGBG are italicized

TABLE 3B

Results obtained with probe for TNFα. Probe ID = 207113_s_at

| | H6-144 | H6-145 | H6-17 | H6-4 | H6-71 | H5-1293 | H5-1294 | H5-1327 | H5-1333 |
|---|---|---|---|---|---|---|---|---|---|
| MGBG | 518.3 | 333.2 | 519.6 | 64.9 | 718.3 | 180.8 | 2,954 | 76.4 | 230.5 |
| ON | 258.6 | 385.7 | 840.8 | 67.6 | 153.9 | 236.9 | 29.5 | 50.3 | 240.2 |
| Ratio MG BG/ON | 2.00 | 0.86 | 0.62 | 0.96 | 4.67 | 0.76 | 100.1 | 1.52 | 0.96 | samples not significantly changed in the presence of MGBG are italicized

TABLE 4A

Results obtained with probe for IL10, Probe ID = 207433_at

| | C6-139 | C6-146 | C6-19 | C6-186 | C6-187 | M6-177 |
|---|---|---|---|---|---|---|
| MGBG | 61.5 | 414.6 | 190.2 | 623.6 | 279.1 | 261.6 |
| ON | 166.9 | 195.3 | 71.2 | 345.8 | 458.3 | 492.2 |
| Ratio MGBG/ON | 0.37 | 2.12 | 2.67 | 1.80 | 0.61 | 0.53 | samples not significantly changed in the presence of MGBG are italicized

TABLE 4B

Results obtained with probe for IL10, Probe ID = 207433_at

| | H6-144 | H6-145 | H6-17 | H6-4 | H6-71 | H5-1293 | H5-1294 | H5-1327 | H5-1333 |
|---|---|---|---|---|---|---|---|---|---|
| MGBG | 91.7 | 160 | 60.9 | 93.5 | 311.8 | 72.2 | 167.9 | 80.6 | 95.4 |
| ON | 74.8 | 13.7 | 359.4 | 56.9 | 12.7 | 16.7 | 58 | 3.5 | 13.3 |
| Ratio MGBG/ON | 1.23 | 11.68 | 0.17 | 1.64 | 24.55 | 4.32 | 2.89 | 23.03 | 7.17 | samples not significantly changed in the presence of MGBG are italicized

Of all the genes that had changes in their average signals in the presence of MGBG, six genes were selected for further analysis. Four of the genes were downregulated in the presence of MGBG and these included Fc gamma receptor I A (FCGR1a or the high affinity IgG receptor or CD64), leukocyte immunoglobulin-like receptor, subfamily A (with TM domain), member 1 (LILRA1 also designated LIR6 or CD85 I), osteopontin (or secreted phosphoprotein 1 or SPP1), and secretogranin V or secretory granule neuroendocrine protein 1 (SGNE1). Two of the proteins had increased signals in the presence of MGBG and these included adenosine deaminase (ADA) and interleukin 24 (IL24). The signals obtained in the microarray experiments with these six genes are presented in Table 5. The calculated fold change obtained in each sample is presented in Table 6. FCGR1A and LILRA1 are down-regulated more than 2 fold by MGBG in 6 of 9 and 5 of 9 HIV samples, respectively, but not in control samples which had much more variable changes than HIV infected individuals. SPP1 and SGNE1 exhibit 2 fold or greater reductions in signals in 12 and 13 of the 15 samples evaluated. Also note the lack of contrary changes. ADA is consistently up-regulated by MGBG in all samples tested. IL24 is upregulated after MGBG exposure in HIV infected samples but not controls. Accordingly these six genes were further evaluated by quantitative real-time reverse-transcriptase PCR.

Example 2: Quantitative RT-PCR Confirmation of Genes Affected by MGBG

To evaluate the effect of MGBG on gene expression, blood samples were obtained from patients (N=18, 10 HIV-infected and 8 Healthy Controls). Mononuclear cells were isolated via Percoll gradient centrifugation. The cells were split into two tubes, one treated with 10 µM of MGBG and the other non-treated. The cells were then cultured overnight in RPMI media plus 10% fetal bovine serum at 37 C under non-adherent conditions, collected, lysed using Trizol solution, and total RNA prepared according to manufacturer's instructions (Invitrogen, Carlsbad, Calif.).

Approximately 200 ng of total RNA prepared from each sample was converted to cDNA using the First Strand cDNA Synthesis Kit for RT-PCR [AMV] kit (Roche Applied Diagnostics, Indianapolis, Ind.) according to manufacturer's instructions. Around 5 ng of cDNA sample was then used for PCR performed on a LightCycler (Roche Applied Diagnostics, Indianapolis, Ind.) using the LightCycler FastStart DNA Master SYBR Green I kit. PCR conditions are as

TABLE 5

Signals obtained with 6 most consistently changed genes

| Sample | FCGR1a + | FCGR1a − | LILRA1 + | LILRA1 − | SPP1 + | SPP1 − | SGNE1 + | SGNE1 − | ADA + | ADA − | IL24 + | IL24 − |
|---|---|---|---|---|---|---|---|---|---|---|---|---|
| H5-1293 | 264 | 2416 | 21 | 137 | 64 | 3875 | 14 | 45 | 1845 | 578 | 350 | 65 |
| H5-1294 | 33 | 142 | 1 | 18 | 22 | 9523 | 8 | 488 | 4290 | 84 | 1364 | 247 |
| H5-1327 | 14 | 38 | 15 | 37 | 1684 | 2276 | 79 | 188 | 832 | 231 | 59 | 23 |
| H5-1333 | 347 | 874 | 164 | 81 | 487 | 2789 | 44 | 130 | 5472 | 376 | 577 | 127 |
| H6-004 | 415 | 917 | 40 | 44 | 1480 | 8780 | 17 | 751 | 769 | 130 | 111 | 25 |
| H6-017 | 461 | 201 | 129 | 369 | 113 | 7689 | 7 | 1039 | 6724 | 3365 | 85 | 3376 |
| H6-071 | 59 | 723 | 10 | 148 | 34 | 1938 | 10 | 99 | 6874 | 376 | 1940 | 10 |
| H6-144 | 800 | 1012 | 65 | 413 | 143 | 247 | 13 | 40 | 1964 | 839 | 178 | 294 |
| H6-145 | 1561 | 2078 | 246 | 187 | 458 | 2772 | 12 | 80 | 7488 | 336 | 375 | 14 |
| Average | 439 | 933 | 77 | 159 | 498 | 4432 | 23 | 318 | 4029 | 702 | 560 | 465 |
| C6-019 | 136 | 40 | 73 | 1055 | 53 | 5314 | 13 | 1603 | 5384 | 1509 | 578 | 2035 |
| C6-139 | 51 | 91 | 42 | 313 | 81 | 1972 | 2 | 265 | 2900 | 1014 | 206 | 173 |
| C6-146 | 612 | 188 | 99 | 191 | 264 | 988 | 3 | 33 | 5895 | 1055 | 1549 | 474 |
| C6-186 | 53 | 46 | 94 | 344 | 232 | 1629 | 45 | 208 | 5781 | 1559 | 925 | 788 |
| C6-187 | 1362 | 68 | 212 | 647 | 1519 | 3456 | 13 | 122 | 6428 | 1519 | 163 | 748 |
| M6-177 | 1435 | 494 | 277 | 3219 | 1647 | 1080 | 2 | 112 | 6731 | 2104 | 166 | 360 |
| Average | 608 | 155 | 133 | 962 | 633 | 2407 | 13 | 391 | 5520 | 1460 | 598 | 763 |

TABLE 6

Fold changes of six most consistently changed genes.

| Gene: | H5-1293 | H5-1294 | H5-1327 | H5-1333 | H6-4 | H6-17 | H6-71 | 116-144 | H6-145 | C6-139 | C6-146 | C6-19 | M6-177 | C6-186 | C6-187 |
|---|---|---|---|---|---|---|---|---|---|---|---|---|---|---|---|
| Down-regulated genes in MGBG: ON/MGBG ratio | | | | | | | | | | | | | | | |
| FCGR1A | 9.2 | 4.3 | 2.7 | 2.5 | 2.2 | 0.4 | 12.3 | *1.0* | *0.9* | *1.3* | 0.3 | 0.3 | 0.3 | *0.9* | 0.1 |
| LILRA1 | 6.5 | 13.8 | 2.4 | 0.5 | *1.1* | 2.9 | 14.6 | *1.3* | *1.3* | *1.8* | 0.3 | 0.3 | 11.6 | 3.7 | 3.1 |
| SPP1 | 60.5 | 438.8 | *1.4* | 5.7 | 5.9 | 68.0 | 57.9 | 4.2 | *1.2* | 47.8 | 11.5 | 43.9 | *0.7* | 7.0 | 2.3 |
| SGNE1 | 3.3 | 58.8 | 2.4 | 3.0 | 45.5 | 159.8 | 10.1 | 63 | 0.8 | 7.4 | *1.9* | 14.4 | 53.3 | 4.7 | 9.3 |
| Up-regulated genes in MGBG: MGBG/ON ratio | | | | | | | | | | | | | | | |
| ADA | 3.2 | 51.2 | 3.6 | 14.6 | 5.9 | 2.0 | 18.3 | 2.3 | 22.3 | 2.9 | 5.6 | 3.6 | 3.2 | 3.7 | 4.2 |
| IL24 | 5.4 | 5.5 | 2.6 | 4.5 | 4.5 | 0.03 | 192.1 | *0.6* | 26.0 | *1.2* | 3.3 | 0.3 | *0.5* | *1.2* | 0.2 |

Fold change (downregulation in upper panel; upregulation in lower group) in presence of 10 µM MGRC. Italizied values in cells were not significantly changed. Bold numbers indicate samples that had changes in signal of greater than 2 fold in the opposite direction of the majority of samples for a given gene.

follows: 1 cycle of denaturation at 95° C. for 10 minutes, followed by 45 cycles of 95° C. for 10 seconds, 68° C. for 10 seconds, and 72° C. for 16 seconds.

The sequences of gene-specific primers evaluated are listed below. All samples were also amplified with the human β-actin LightCycler-Primer set (Roche Diagnostics).

TABLE 7

Primers employed for Quantitative RT-PCR (QRT-PCR)

| Gene | Forward (5' ---  >) | Reverse (5' ---  >) |
|---|---|---|
| G1P3 | AGCAGCGTCGTCATAGGTAAT<br>SEQ ID NO: 1 | ACAGGAGGATCACTTGAGGCT<br>SEQ ID NO: 2 |
| TGFB1 | CCAGCATCTGCAAAGCTCC<br>SEQ ID NO: 3 | TTGTACAGGGCCAGGACCTT<br>SEQ ID NO: 4 |
| CSF3R | TGTTCGGCCTCCTGCTGTT<br>SEQ ID NO: 5 | GCTTCTTTTCATCCTCCTCCA<br>SEQ ID NO: 6 |
| GPR43 | TGCTACGAGAACTTCACCGAT<br>SEQ ID NO: 7 | GAAGCACACCAGGAAATTGA<br>SEQ ID NO: 8 |
| MX2 | TCTTCCCTGACCTTCACGAA<br>SEQ ID NO: 9 | CATTTATTAAGCAGTTACAATGCTG<br>SEQ ID NO: 10 |
| TNFSF10 | CTACCTCATATCAGTTTGCTAGCAG<br>SEQ ID NO: 11 | CGATCTTTTAGTGGTGCCTCTT<br>SEQ ID NO: 12 |
| IFIT2 | CAGTAAAGAGCTTACTCCTGTAGCG<br>SEQ ID NO: 13 | AAGCCTCAGAATCTGCTCCATT<br>SEQ ID NO: 14 |
| FCAR | GACTTTCCCATGCCTTTCAT<br>SEQ ID NO: 15 | ACCGGAATCTGTAGTGCCCTA<br>SEQ ID NO: 16 |
| ORM1 | CGACAGGACCAGTGCATCTAT<br>SEQ ID NO: 17 | AACTCTCCCAGTTGCTCCTT<br>SEQ ID NO: 18 |
| TNFRSF10c | CCCAGCTGCTGAAGAGACAAT<br>SEQ ID NO: 19 | ATGATCCCTACGATGGTGCAT<br>SEQ ID NO: 20 |
| CLECSF7 | GGATAGCTGTTGTTTCAGAGAAAGG<br>SEQ ID NO: 21 | CTTCTCACAAATACTATATGAGGGC<br>SEQ ID NO: 22 |
| GPR86 | AACACGACCATCGTAGGGTGA<br>SEQ ID NO: 23 | TTTGAGGTGATGGTGGGATA<br>SEQ ID NO: 24 |
| CSPG2 | CACCGATGGCCATGTAAATA<br>SEQ ID NO: 25 | TGTCCAGGAAAAGCCATCTT<br>SEQ ID NO: 26 |
| CD14 | TGGAACAGGTGCCTAAAGGA<br>SEQ ID NO: 27 | ACAGGGTCGAACGTGCACA<br>SEQ ID NO: 28 |
| NBS1 | TGAATGAGGAGTTCTGGTACCT<br>SEQ ID NO: 29 | AGTCAAGCCACAGACTAGGTGTAA<br>SEQ ID NO: 30 |
| CHI3L1 | ACACAGATTTGAGCTCAGCCC<br>SEQ ID NO: 31 | ATGTTTGGCTCCTTGGTGAT<br>SEQ ID NO: 32 |
| CLEC4E | AGGTATTAAGCCCAGTGCCTAA<br>SEQ ID NO: 33 | GAAAATTATGTCTTTTGTGGGAACA<br>SEQ ID NO: 34 |
| SIGLEC5 | TTTCTGAGATGAAGTCGAGGG<br>SEQ ID NO: 35 | TCTGCTTGGAGCACTTAAACA<br>SEQ ID NO: 36 |
| GPR109B | AATTGTGTTGCTCCTGGAGGA<br>SEQ ID NO: 37 | CAATGCCATTTCCTTTCCCA<br>SEQ ID NO: 38 |
| TNFa | Quantitect cat # QT01079561 | 104 by amplicon |
| 1Qgag | TTGCCCATGGTTTCCAGAACAAG<br>SEQ ID NO: 39 | GGGATTTTTTCCTTGTGTTTTCA<br>SEQ ID NO: 40 |
| 8pGAG | AGTATGGATCTCAGGCGGT<br>SEQ ID NO: 41 | CATCGGTTGTAACATTACC<br>SEQ ID NO: 42 |
| PI3 | ATGGCCTTAGCTCTTAGCCAA<br>SEQ ID NO: 43 | GCTCTTGCGCTTTGACTTTA<br>SEQ ID NO: 44 |
| IL1RN | AGACCTTCTATCTGAGGAACAACCA<br>SEQ ID NO: 45 | TTGTCCTGCTTTCTGTTCTCG<br>SEQ ID NO: 46 |

TABLE 7-continued

Primers employed for Quantitative RT-PCR (QRT-PCR)

| Gene | Forward (5' --- >) | Reverse (5' --- >) |
|---|---|---|
| IL6 | TCCACTGGGCACAGAACTTAT SEQ ID NO: 47 | TCTGGCTCTGAAACAAAGGA SEQ ID NO: 48 |
| IL1A | TGCCTTCTGCTTTTAAGTTGC SEQ ID NO: 49 | GATGAAGGGGTTCCCATAAA SEQ ID NO: 50 |
| SPP1 | AGCCACAAGCAGTCCAGATTAT SEQ ID NO: 51 | TTGACCTCAGAAGATGCACTATC SEQ ID NO: 52 |
| FCGR1A | ACTCTGGGTTATACTGGTGCGA SEQ ID NO: 53 | CCAAAGAGATTTCTAAATCCCAC SEQ ID NO: 54 |
| SGNE1 | TCCCTGTGAATGACAGCATGT SEQ ID NO: 55 | AAACTGCAAGAAATCTGAGCC SEQ ID NO: 56 |
| LILRA1 | CAGTCAGGCAGAAGTATGCAAA SEQ ID NO: 57 | TCCCTTTGTCCTAGAAAGTTGAGG SEQ ID NO: 58 |
| ADA | GCTACCACACCCTGGAAGA SEQ ID NO: 59 | CCGTTTGGTCATCTGGTAATC SEQ ID NO: 60 |
| IL24 | AACAGAGAGGGATGCTTGGAT SEQ ID NO: 61 | CACCAAGGGAAAGGGATGAT SEQ ID NO: 62 |

Of the genes evaluated, MGBG has the biggest effect on SPP1 (Table 8). It consistently down-regulates SPP1 levels in all of the unsorted samples looked at, with fold changes between the untreated and the treated of up to 300 in certain samples. IL1RN seems to be down-regulated, though not as consistently (15 out of 18 samples) as SPP1. SGNE3 also seems to be mostly down-regulated, although the level of inhibition in most samples is low. Genes that are up-regulated by MGBG include ADA and IL24. ADA is strongly induced and is upregulated in all but one sample. IL24 did not exhibit a consistent pattern of change in the presence of MGBG (Table 8). These results are in contrast to the results obtained by QRT-PCR with many other genes, of which results with 6 genes whose transcription appears unaffected by MGBG are presented in Table 9. Thus the effects of MGBG on osteopontin and adenosine deaminase are highly specific.

TABLE 8

Fold change of 5 genes Identified by microarray by QRT-PCR

| | Down-regulated Genes | | | Up-regulated Genes | |
|---|---|---|---|---|---|
| Sample | SPP1 | IL1RN | SGNE3 | IL24 | ADA |
| H1293 | −18.90 | −4.92 | 1.79 | 2.50 | 3.01 |
| H1294 | −300.25 | −2.31 | −7.11 | −2.41 | 3.76 |
| H1327 | −2.14 | −8.28 | −2.50 | −1.48 | 1.16 |
| H1333 | −18.90 | −17.75 | −4.41 | −1.30 | 7.16 |
| H6_4 | −20.11 | −10.41 | 1.58 | 5.35 | 16.80 |
| H6_17 | −83.87 | −3.73 | −3.25 | 1.20 | 4.69 |
| H6_71 | −6.59 | 1.12 | −1.30 | 1.09 | 18.77 |
| H6_144 | −1.30 | −1.73 | −2.39 | −1.13 | 2.33 |
| H6_145 | −8.82 | −1.36 | −2.43 | 1.12 | 13.00 |
| H1334 | −95.67 | −14.22 | | 11.88 | 3.34 |
| C6_139 | −7.89 | −1.87 | −1.48 | 2.57 | 5.90 |
| C6_146 | −1.95 | −1.78 | 1.61 | 2.55 | 10.06 |
| C6_19 | −46.21 | 8.63 | −3.61 | 2.25 | 7.52 |
| C6_186 | −5.90 | −2.27 | −1.66 | 1.01 | 4.23 |
| C6_187 | −2.11 | 1.59 | −1.13 | −1.17 | 7.21 |
| C5_75 | −6.15 | −8.17 | | 1.92 | 1.38 |
| C5_76 | −1.28 | −19.56 | | 1.32 | −0.73 |
| C5_78 | −467.88 | −1.77 | | 1.79 | 6.68 |
| AVERAGE | −60.9 | −4.9 | −1.9 | 1.6 | 6.5 |

TABLE 8-continued

Fold change of 5 genes Identified by microarray by QRT-PCR

| | Down-regulated Genes | | | Up-regulated Genes | |
|---|---|---|---|---|---|
| Sample | SPP1 | IL1RN | SGNE3 | IL24 | ADA |
| STDEV | +/−124.2 | +/−7.1 | +/−2.5 | +/−3.2 | +/−5.3 |
| MIN | −467.9 | −19.6 | −7.1 | −2.4 | −0.7 |
| MAX | −1.3 | 8.6 | 1.8 | 11.9 | 18.8 |
| % >2 fold Changed | 83% | 55% | 50% | 33% | 83% |

Table 8 shows the genes affected by MGBG in the unsorted samples. The numbers represent the fold change between the untreated and the treated. Negative numbers indicate fold reduction and the positive numbers represent fold increase changes. Samples that were not evaluated with a particular gene are shaded grey. Significant reductions or increases (>=2 fold) are in bold font. As shown, OPN or SPP1 is highly inhibited after treatment with MGBG.

TABLE 9

Results obtained with six genes that were not affected by MGBG

| Sample | G1P3 | MX2 | IL6 | NBS1 | FCGR1A | LILRA1 |
|---|---|---|---|---|---|---|
| H1293 | −2.85 | 1.13 | 1.74 | −4.35 | −10.78 | 1.34 |
| H1294 | 1.47 | −2.11 | −6.15 | −8.51 | −17.15 | −4.79 |
| H1327 | 1.22 | −2.85 | −1.09 | −2.51 | −2.22 | −1.31 |
| H1333 | −1.66 | 1.23 | −5.46 | −1.89 | −3.86 | 1.28 |
| H6_4 | 1.68 | 6.06 | 14.72 | 3.63 | 1.05 | 13.45 |
| H6_17 | 1.92 | 2.03 | −5.31 | 1.68 | −1.61 | −1.91 |
| H6_71 | −1.25 | −1.09 | 3.71 | 1.25 | −1.84 | 1.01 |
| H6_144 | 1.31 | 1.16 | 1.04 | 1.35 | −1.01 | −3.10 |
| H6_145 | −1.25 | −1.01 | 1.01 | −1.56 | −1.72 | 1.31 |
| H1334 | −2.03 | 4.35 | −2.93 | 2.07 | −3.73 | |
| C6_139 | −1.14 | 1.56 | −4.17 | 3.51 | 1.72 | −2.87 |
| C6_146 | −2.04 | −2.81 | 2.20 | −1.09 | 5.94 | 1.52 |
| C6_19 | 2.13 | 3.07 | 2.83 | 3.51 | 2.39 | −3.97 |
| C6_186 | −1.14 | 1.16 | −2.71 | 1.04 | −1.97 | −2.27 |
| C6_187 | 1.22 | −1.33 | −4.06 | 4.08 | 19.03 | 1.11 |
| C5_75 | −2.99 | −1.77 | 1.74 | 2.31 | 1.16 | |
| C5_76 | −6.63 | −3.27 | 1.30 | 1.14 | −0.41 | |
| C5_78 | −1.95 | 1.36 | 1.46 | 1.27 | −0.43 | |
| AVERAGE | 0.96 | 1.55 | 1.91 | 1.65 | 2.25 | 1.71 |
| STDEV | 0.57 | 1.52 | 3.35 | 1.26 | 4.42 | 3.41 |
| MIN | −6.63 | −3.27 | −6.15 | −8.51 | −17.15 | −4.79 |
| MAX | 2.13 | 6.06 | 14.72 | 4.08 | 19.03 | 13.45 |

Example 3: Evaluation of Changes Induced by MGBG for OPN, ADA and Other Genes The changes induced by MGBG in different blood cell types were determined for osteopontin and adenosine deaminase and 7 other genes. For this experiment, blood samples were obtained from 6 healthy controls (3 men/3 women from 20 to 55 years of age) and mononuclear cells were isolated via Percoll gradient centrifugation. The cells were then incubated for 3 hours in RPMI media plus 10% fetal bovine serum at 37 C. At that point MGBG was added to 10 µM to half of each sample and then the cells were incubated at 37 C for 20 more hours. The cells were then bound to magnetic beads coated with antibodies to human CD16. Bound cells (CD16 expressing) were separated from unbound cells using an AutoMACs according to manufacturer's instructions (Miltenyi, Auburn Calif.). Then CD16+ cells are released from the magnetic beads and both the CD16+ and CD16− cells are combined with magnetic beads coated with antibodies to human CD14. Antibody bound and unbound cells were then separated using the AutoMACs machine. This results in four different cell fractions:

1. Cells that neither express CD16 nor CD14 (the −/− Cells). This is mostly T lymphocytes;
2. Cells that only express CD16. This includes contaminating granulocytes not removed by Percoll centrifugation and CD16+ monocytes with very low CD14 expression;
3. Cells that express both CD16 and CD14. This includes monocytes that are expressing CD16+ and macrophages (which express high levels of both); and
4. Cells that only express CD14. This would include most normal human monocytes.

After separation, cells of each fraction are washed with PBS and the number of viable cells determined by trypan blue exclusion. RNA is then prepared from each cell group using TRIZOL, according to manufacturer's instructions.

The results obtained are presented in FIG. 2. It can be appreciated that of the four cell fractions, the −/− cells are the most numerous with a median yield of 4.2 million cells. Approximately ten fold less CD14+ and double positive cells were isolated (4.7 and $3.8 \times 10^5$ cells, respectively). The lowest number of cells is in the CD16 single positive fraction which had a median yield of $6.0 \times 10^4$ cells. β-actin levels as measured by QRT-PCR accurately reflected cell counts with the highest threshold cycles obtained from the CD16+ cells and the lowest values from the double-negative cells. For osteopontin, the highest β-actin-normalized signals were obtained from CD14+ monocytes and CD14/16++ monocyte and macrophages. Upon exposure to osteopontin RNA levels in the CD14+ monocyte fraction decreased the most with a median reduction of 4.8 fold (0.21 of no MGBG) which was significantly less than 1.0 (no change) by the Wilcoxon signed rank test (p=0.03). In contrast changes induced by MGBG in CD14/16++ cells, CD16+ cells, and double negative cells were 0.61, 1.12, and 0.70, respectively. None of these changes were significantly different than 1.0. Thus, in healthy individuals MGBG exposure reproducibly reduces osteopontin RNA signals in monocytes.

For adenosine deaminase, levels of RNA signal were approximately equal in all four cell fractions (from 1 to 10% of actin levels). Exposure to MGBG resulted in significant increases in ADA transcription in CD14+ monocytes (median change 10.8 fold, p=0.0156). Much lower but still significant changes were seen in CD14/CD16++ cells (median change 2.8 fold). Double negative cells and CD16+ cells did not change significantly. Thus as is the case for osteopontin, RNA changes are primarily seen in monocytes after exposure to MGBG. Smaller changes are also detected in CD14/CD16 double positive cells. Thus monocytes and macrophages are the primary cellular targets of MGBG.

To determine if MGBG treatment might be globally affecting monocytes and macrophages we looked at four additional gene that are known to be highly expressed in monocytes and macrophages. The genes were CD14 (which also provides a level of quality control on our cell separations) and interleukin 1 receptor antagonist (IL1RN), G coupled receptor 43 (GPR43, also known as the free fatty acid receptor), and the cytokine TNFα. For all four genes levels of RNA in monocytes and macrophages ranged between 10 to 100 times greater than that seen in double negative lymphocytes. IL1RN CD14, and TNFα had approximately equal levels of RNA signal in both CD14+ monocytes and CD14/CD16++ macrophages. For GPR43, median RNA levels were 5 to 10 fold higher in CD14/16++ cells relative to CD14+ monocytes. Exposure to MGBG resulted in no clear trend in expression changes. In particular exposure to MGBG significantly lowered RNA signal of TNFα in monocytes (median signal=0.32, p=0.03) but not the signals of the other 3 genes. In contrast exposure to MGBG caused a slight increase in GPR43 expression (median signal=2.4, p=0.03) and a slight decrease in RNA signals for CD14 (median signal=0.55, p=0.02) in CD14/CD16++ macrophages. Thus evaluation of other monocyte and macrophage specific genes did provide evidence for a global and systematic effect of MGBG on gene expression in those cells. Thus the more profound effects of MGBG on osteopontin and adenosine deaminase are specific.

Example 4: Effect of MGBG on Osteopontin Protein Secretion

Peripheral Blood Mononuclear Cells (PBMCs) were isolated from patients diagnosed with Amyotrophic Lateral Sclerosis (ALS), Alzheimer's Disease (AD), Human Immunodeficiency Virus (HIV), Breast Cancer, AIDS Dementia, and healthy donors. The heparinised blood was mixed with equal volumes of sterile phosphate-buffered saline ($Ca^{++}$, $Mg^{++}$ free PBS) and layered over Percoll (Amersham Biosciences, Piscataway, N.J.) at 1.087 g/ml. The cells were centrifuged and the mononuclear cell layer was collected. The PBMCs were cultured in a concentration of $1 \times 10^6$ cells/ml in non-adherent conditions in polypropylene tubes containing complete media (RPMI 1640, 10% fetal bovine serum (HyClone, Logan, Utah), 1% Sodium Pyruvate) and incubated in a 5% $CO_2$, 37° C. humidified incubator. The cells were grown in the presence of 0 µM, 0.1 µM, 1 µM, 10 µM, or 100 µM MGBG plus complete media and the cell culture supernatants (CCS) were isolated on the fifth day and frozen at −20° C. until ready to be tested. Human Osteopontin (OPN) levels were measured with the Human Osteopontin ELISA kit (R&D Systems, Inc., Minneapolis, Minn.) according to manufacturer's instructions. The CCS were tested in duplicate and the Magellan v. 4.0 software (Salzburg, Austria) was used to analyze the results.

The average OPN levels (ng/ml) in 0 µM, 0.1 µM, 1 µM, 10 µM, and 100 µM MGBG were measured. The results are depicted in FIGS. 3-7 as a graph comparing diseased sample with normal sample. In FIGS. 3-7, each point on the graph is the average of each sample with standard error represented as error bars. The solid lines represent diseased cells and the dashed lines represent normal cells.

Figure 3:
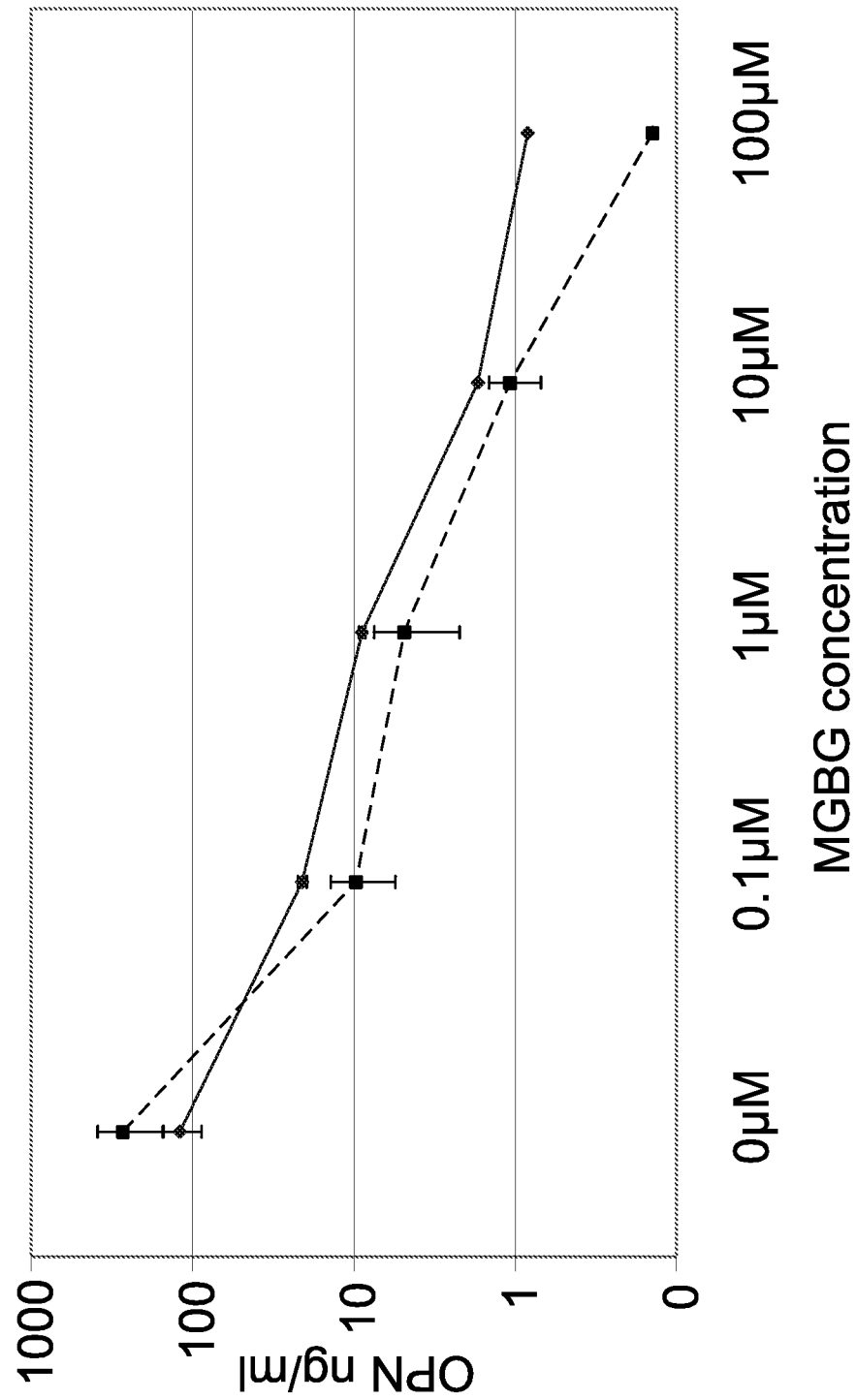
FIG. 3 depicts the average OPN levels in CCS of breast cancer and normal PBMCs treated with MGBG.
Figure 4:
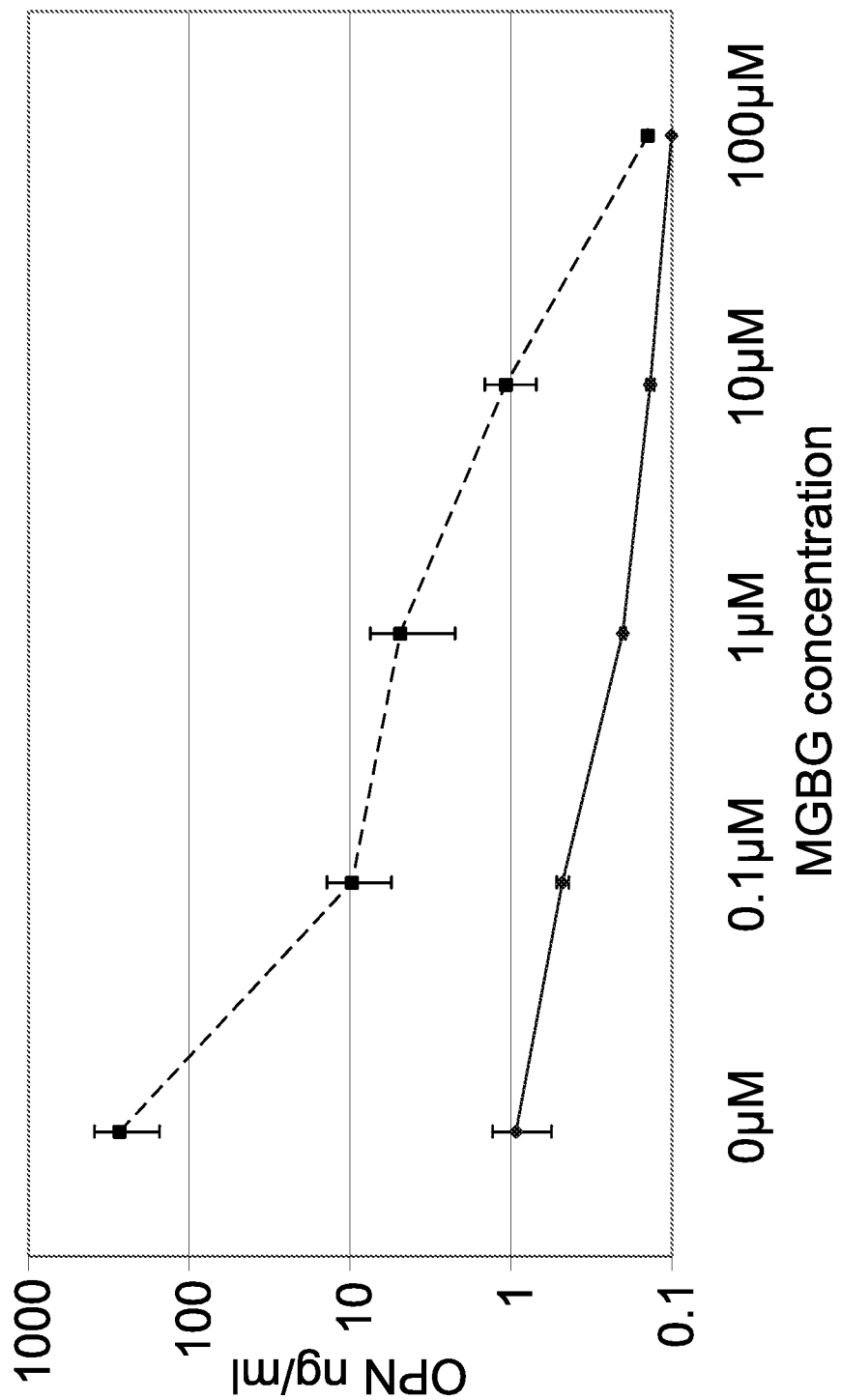
FIG. 4 depicts the average OPN levels in CCS of AD and normal PBMCs treated with MGBG.
Figure 5:
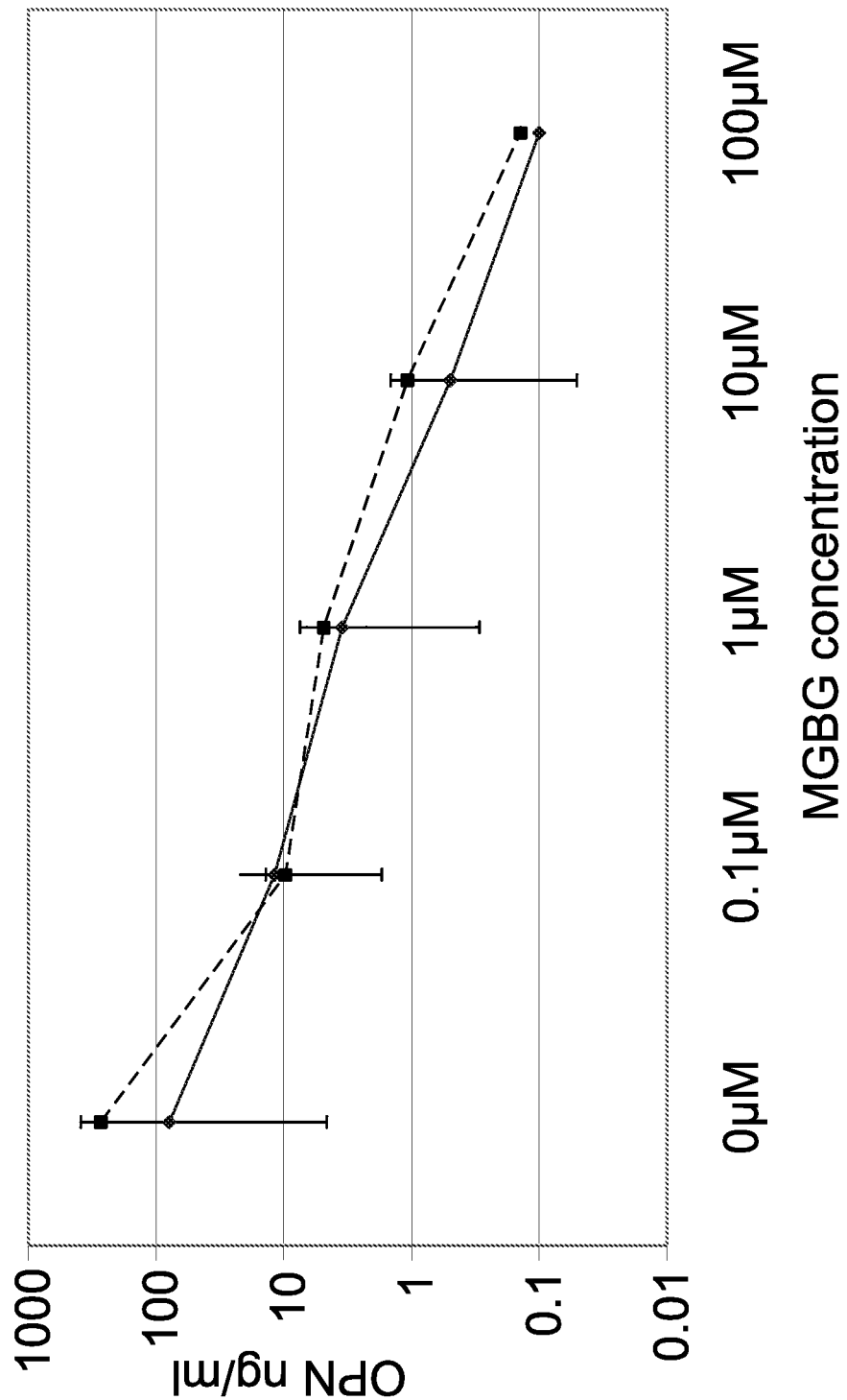
FIG. 5 depicts the average OPN levels in CCS of HIV and normal PBMCs treated with MGBG.

The average OPN levels obtained from the CCS of healthy/normal samples (n=3) were 270, 9.69, 4.85, 1.07, and 0.14 ng/ml in cultures with 0 µM, 0.1 µM, 1 µM, 10 µM, and 100 µM MGBG, respectively. The corresponding average OPN levels obtained from the CCS of breast cancer samples (n=3), as shown in FIG. 3, were 125.96, 20.89, 8.87, 2.12, and 0.84 ng/ml. The corresponding average OPN levels obtained from the CCS of the AD sample (n=1), as shown in FIG. 4, were 0.926, 0.477, 0.201, 0.136, and 0 ng/ml. For AD, each point on the graph is the average of the duplicates tested on the ELISA plate. The corresponding average OPN levels obtained from the CCS of HIV samples (n=2), as shown in FIG. 5, were 78.698, 11.833, 3.481, 0.447, and 0 ng/ml.

Figure 6:
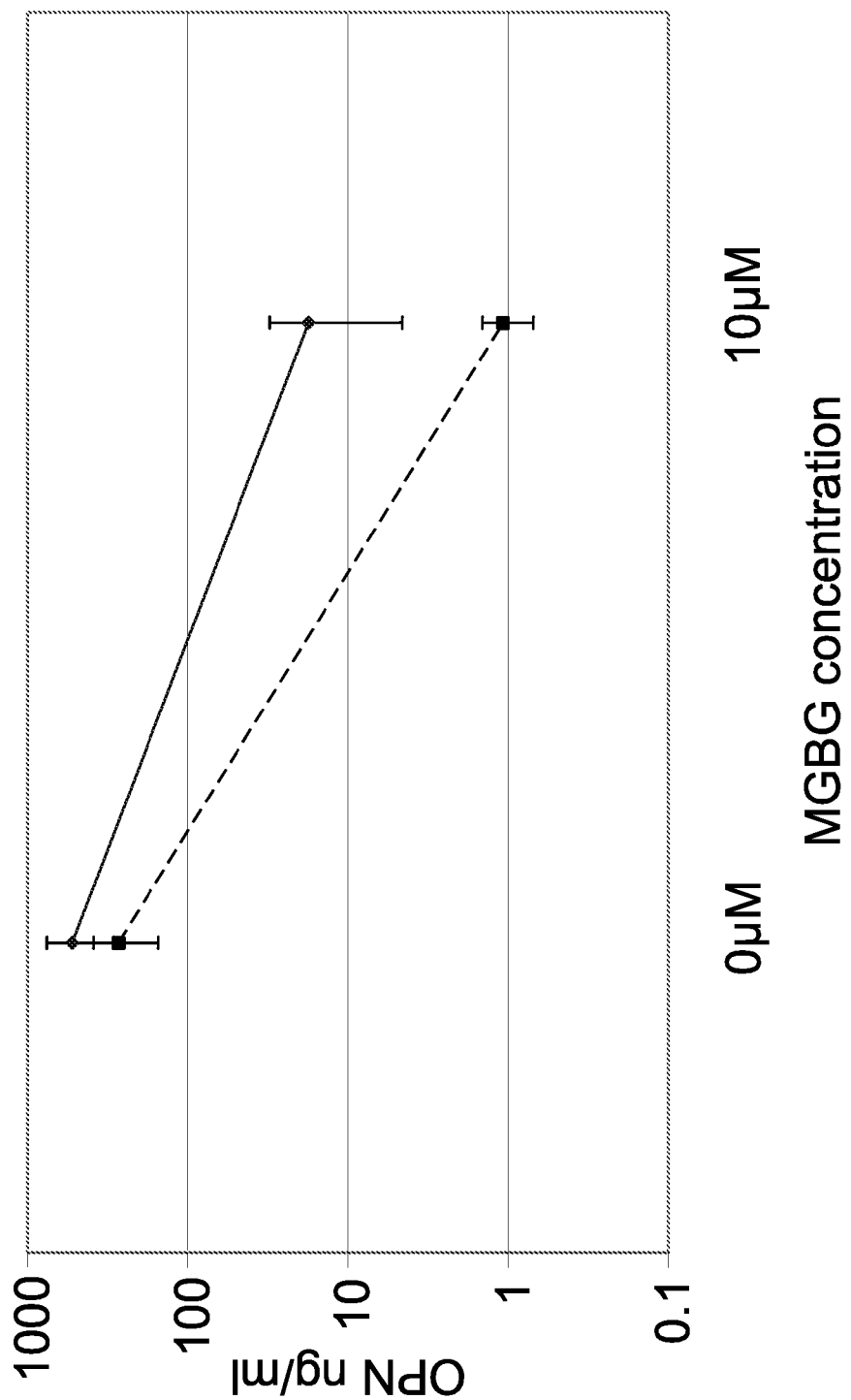
FIG. 6 depicts the average OPN levels in CCS of ALS and normal PBMCs treated with MGBG.
Figure 7:
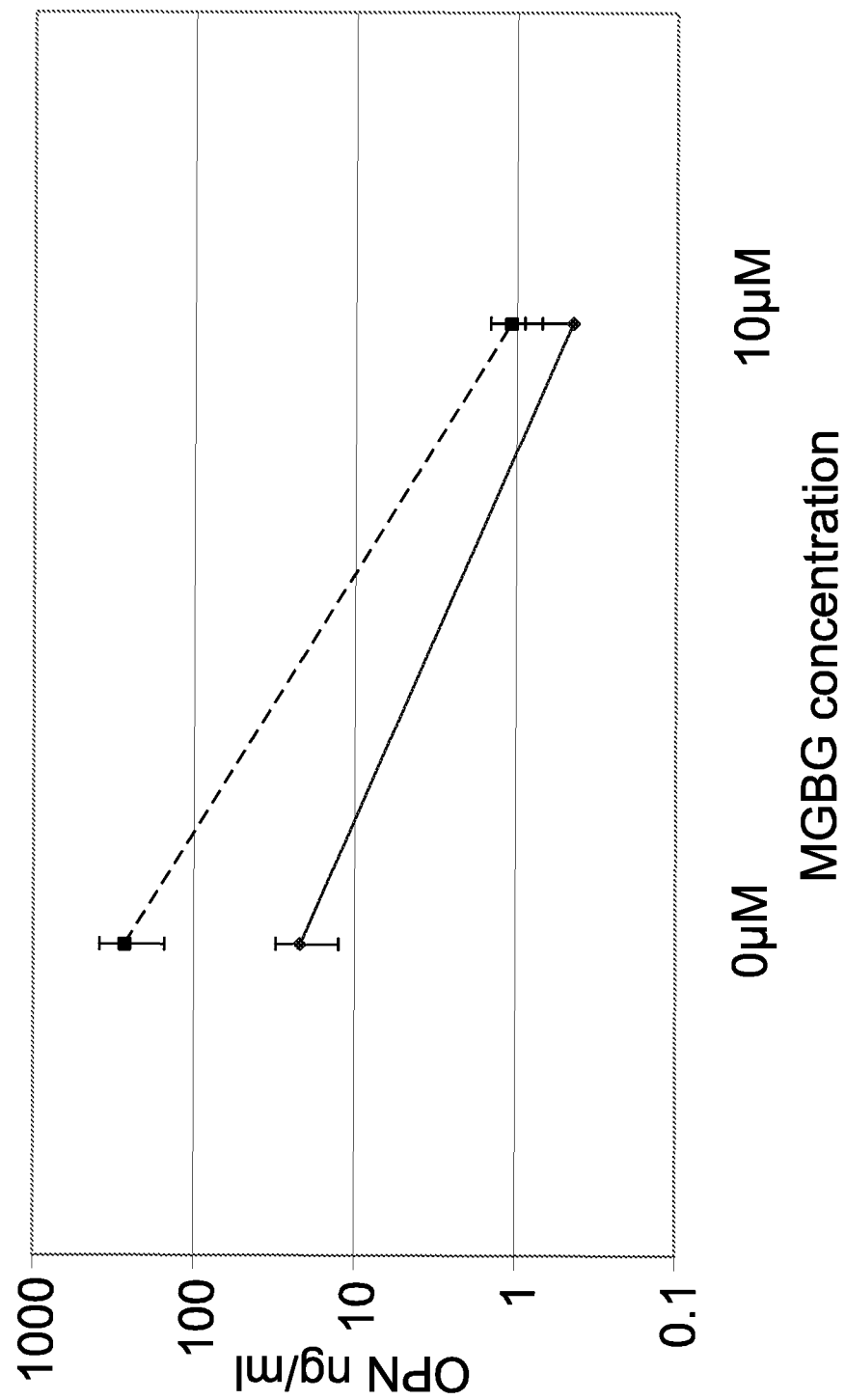
FIG. 7 depicts the average OPN levels in CCS of AIDS dementia and normal PBMCs treated with MGBG.

PBMCs obtained from ALS and AIDS Dementia patients were tested with 0 µM and 10 µM only. The average ALS (n=2) CCS values, as shown in FIG. 6, were 525.644 (0 µM) and 17.669 (10 µM); and the average AIDS Dementia CCS (AIRL2005-374) value, as shown in FIG. 7, was 30.958 (0 µM) and 0.8905 (10 µM). Cell viability data showed that the cells at each MGBG concentration were at least 75% viable when the CCS were collected.

Additionally, cells being targeted by MGBG were investigated. Phenotypic analysis showed that increasing concentrations of MGBG resulted in decreasing yields of CD14+ macrophages but did not affect levels of CD16+/CD14− cells. To elucidate the effects of MGBG and OPN on cell motility, migration assays were conducted. MGBG at 10 µM inhibited macrophage Osteopontin production from >200 ng/mL to nondetectable levels while simultaneously inhibiting HeLa cell invasion into a Matrigel matrix. The results show that MGBG inhibits OPN production of mononuclear cells in vitro and that inhibition of OPN by MGBG is sufficient to inhibit cell migration.

Example 5: Effect of Removing Extracellular Osteopontin on Macrophage Differentiation To observe the effects of OPN blocking antibody on macrophage activation, 10 µg of antibody (Immuno-Biological Laboratories, Inc., Minneapolis, Minn.) was added to non-adherent PBMC cultures for 24 and 72 hours. The cells were labeled with mouse anti-human CD14-TriColor (Invitrogen, Carlsbad, Calif.) and mouse anti-human CD16-FITC (fluorescein isothiocyanate; Dako, Carpinteria, Calif.) according to the manufacturer's suggestion; an isotype control was also used. CD14+ monocytes and CD14+/CD16+ macrophages were analyzed by flow cytometry at 24 and 72 hours after cell isolation (BD FACScan, San Jose, Calif. with FACS Express 3 software). Results showed that incubation with neutralizing osteopontin antibody increased the yield of CD14+ monocytes 5.9 fold at 24 hours (2.5% CD14+ in presence of SPP1 Ab vs 0.4% with control Ab) and 16.9 fold at 72 hours (3.7% CD14+ vs 0.2%). Additionally, at 24 hours the yield of CD14/16++ macrophages was reduced 4.5 fold in the presence of neutralizing osteopontin antibodies (0.6% vs 2.5% in presence of control Ab). Additionally CD14/16++ cells isolated in the presence of osteopontin neutralizing antibodies never achieved the typical increase in side scatter seen under normal conditions. Thus removal of osteopontin prevents normal macrophage differentiation and increases the prevalence of CD16− monocytes.

Example 6: Effect of Adding Exogenous OPN on Macrophage Yield

Figure 8:
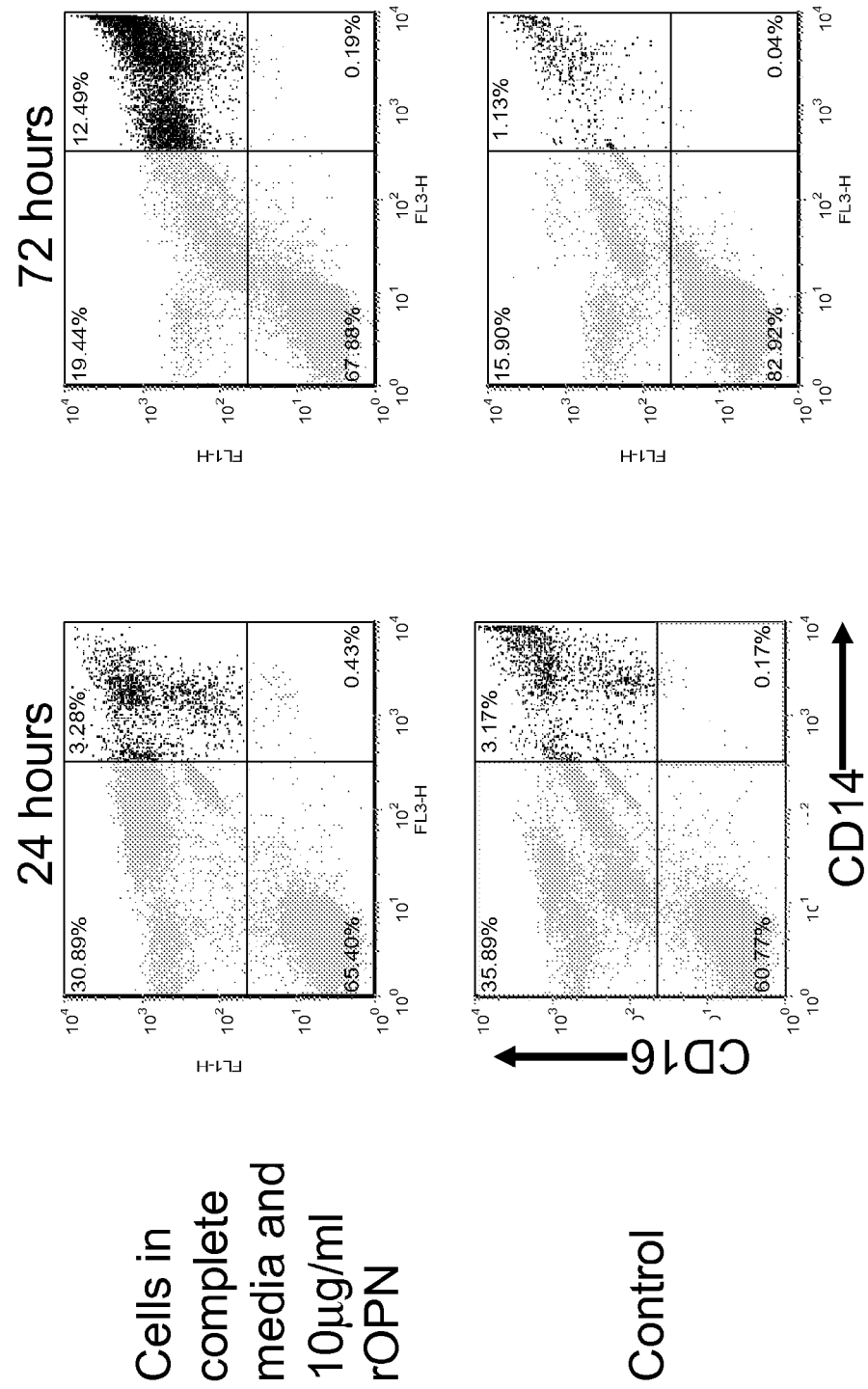
FIG. 8 shows that rOPN increases CD14+/CD16+ cell population.

To determine the role of exogenous recombinant human OPN (rOPN) in macrophage activation, 10 µg/ml rOPN (R&D Systems, Inc., Minneapolis, Minn.) was added to non-adherent PBMC cultures grown in complete or in serum free medium for 24 and 72 hours, and analyzed via flow cytometry. The cells were labeled with α-axis) mouse anti-human CD14-TriColor (Invitrogen, Carlsbad, Calif.) and (y-axis) mouse anti-human CD16-FITC (fluorescein isothiocyanate; Dako, Carpinteria, Calif.) according to the manufacturer's suggestion. As seen in FIG. 8, rOPN increases CD14+/CD16+ cell population. At 24 hours, cells incubated with rOPN in complete medium had no significant accumulation of CD14+/CD16+ cells in comparison to control (no rOPN in the medium). However, at 72 hours a 11-fold increase in CD14+/CD16+ cells were observed in cells incubated with rOPN in comparison to control. A 2.97-fold increase in CD14+/CD16+ cells was also observed with cells cultured with rOPN for 72 hours in serum free conditions in comparison to serum free control. Shown in the upper right quadrant in FIG. 8 is the percentage of cells that are double positive for CD14 and CD16 surface markers.

Example 7: Osteopontin Induces Increased Macrophage Activation and Cytokine Secretion We investigated macrophage activation via flow cytometry and levels of pro- and anti-inflammatory cytokines in cell culture supernatants of mononuclear cells. 10 µg/ml recombinant human OPN (rOPN) was added to mononuclear cells cultured for 3 days, with and without fetal bovine serum (FBS) in cell culture medium, and analyzed via flow cytometry. At 24 hours, cells incubated with rOPN and FBS had no significant accumulation of CD14+/CD16+ cells in comparison to FBS-only control. However, at 72 hours, a 12-fold increase in CD14+/CD16+ cells were observed in cells incubated with rOPN in comparison to control. An increase in CD14+/CD16+ cells was also observed with cells cultured in serum free medium and rOPN in comparison to control. To observe the effects of OPN neutralizing antibody on macrophage activation, 10 µg of antibody was added to cultures for 3 days. The amount of CD14+/CD16+ cells was inhibited by 3.97-fold at 24 hours and 3.76-fold at 72 hours. We also investigated the levels of pro- and anti-inflammatory cytokines in all cell culture supernatants of each time point. On average, IL-6, IL-1β, TNF-α, IL-10, and IL-12p40 were at least 50-fold higher with rOPN at 24 and 72 hours in all culture conditions in comparison to control. IL-12p70 and IL-4 levels had no significant difference at any time point and culture condition. In conclusion, we have found that rOPN increased macrophage activation by the third day. Heightened levels of most of the cytokines measured were also observed when the cells were exposed to rOPN, suggesting that OPN induces mononuclear cells to secrete these cytokines.

Example 8: Effect of MGBG on Osteopontin In Vivo

Many chronic diseases are associated with elevation in osteopontin production in diseased tissues. In order to test whether MGBG, which regulates OPN production in vitro, would have the same effect in vivo, an animal model study was performed. Simian immunodeficiency virus (SIV) infected rhesus macaques develop AIDS and a macrophage infiltrative process of the brain associated dementia within months after infection. MGBG was used in two trials in SIV-infected animals. Rhesus macaques were infected with SIVmac251 and depleted of CD8+ T lymphocytes by administration of a humanized CD8-depleting antibody. This resulted in a rapid depletion of CD8+ T lymphocytes and a very rapid viral infection with a short time course to AIDS. These monkeys were then treated with MGBG as described.

In the first trial three animals (2 treated and 1 untreated) were used. The animals that were treated with MGBG were initially given 200 mg/m² MGBG, and then treated 7 and 14 days later with 300 mg/m² and 400 mg/m², respectively of MGBG. While the untreated animal developed SIVE by the third week, the treated animals showed no indications of SIVE or DRG infiltration. The trial was halted when the treated animals developed severe GI toxicity at an MGBG dose of 400 mg/m².

In the second trial 2 treated and 2 untreated animals were used. In this trial the animals were treated with a bi-weekly dosing of 250 mg/m² MGBG. The untreated animals were SIVE+ in 50 days post-infection and developed AIDS/SIVE within 85 days. The treated animals showed no evidence for SIV disease. Further, no drug related toxicity was seen through 8 cycles of MGBG.

Figure 9:
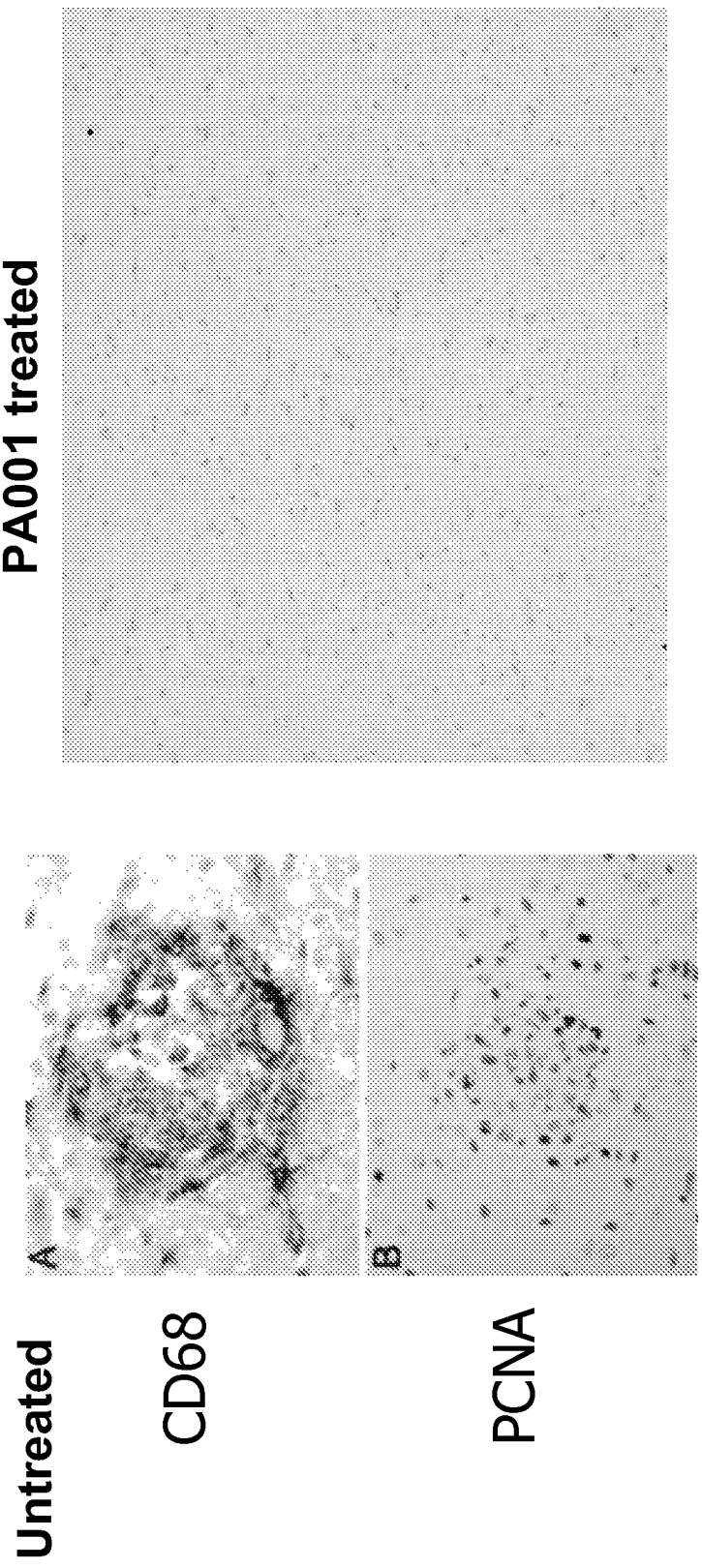
FIG. 9 shows the results with, and without MGBG (PA001) treatment in infected macaques on macrophages in CNS.

In both trials, the infected untreated animals developed AIDS and dementia, but none of the treated animals became ill. FIG. 9 shows that in the infected, untreated animal brains, characteristic macrophage infiltration was observed, but with MGBG (PA001) treatment, no pathology was observed. SIV-infected macaques treated with 4 doses of MGBG (PA001) demonstrated absence of SIV-associated macrophages in the frontal cortex compared to non-treated.

Figure 10:
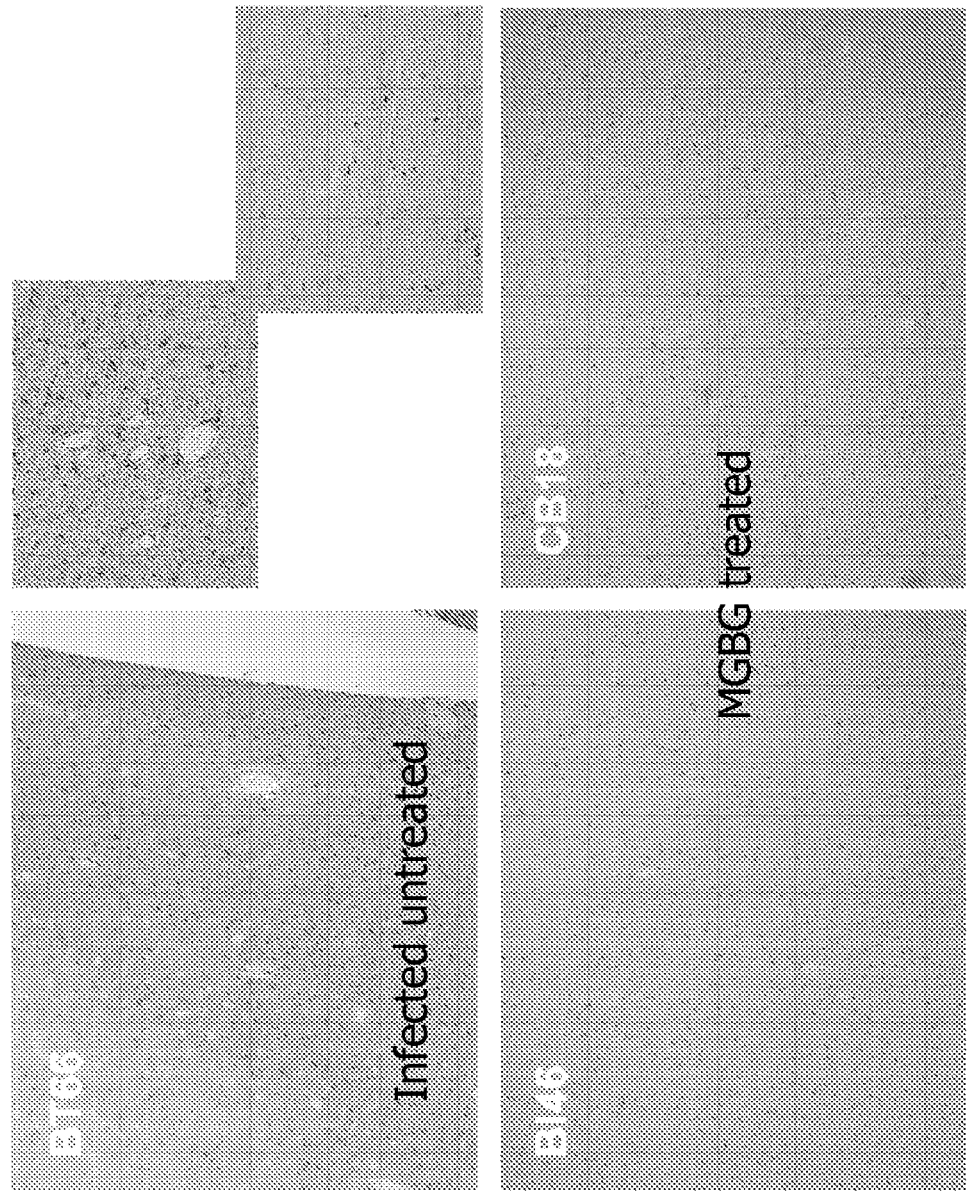
FIG. 10 shows the OPN levels in brains of SIV-infected animals with, and without, MGBG treatment.
Figure 11:
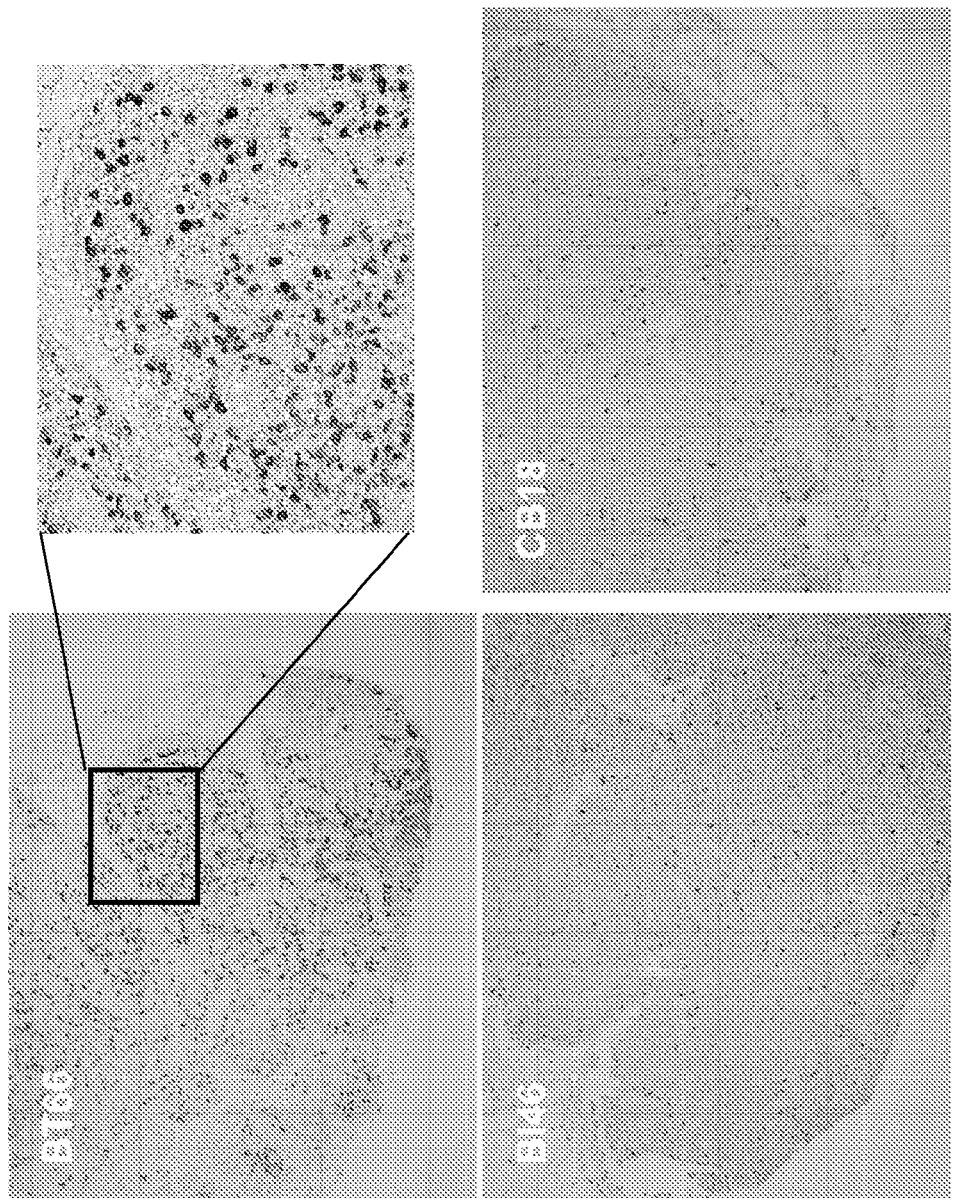
FIG. 11 shows the OPN levels in lymph nodes of SIV-infected animals with, and without, MGBG treatment. Samples B146 and CB18 were treated with MGBG, whereas BT66 was not.

These same brains stained with an antibody to OPN, showed that treatment was associated with complete removal of OPN whereas the infected uninfected animal's brain had large concentrations of OPN (FIG. 10). Similarly, as shown in FIG. 11, lymph nodes from the animals showed differential levels of OPN staining with treatment (B146 and CB18) associated with markedly decreased levels of OPN. These results show that MGBG treatment of an OPN associated disease turns off OPN production in vivo with associated reversal of pathologic processes.

Example 9: Effect of MGBG on Osteopontin RNA and Protein Production

Figure 12:
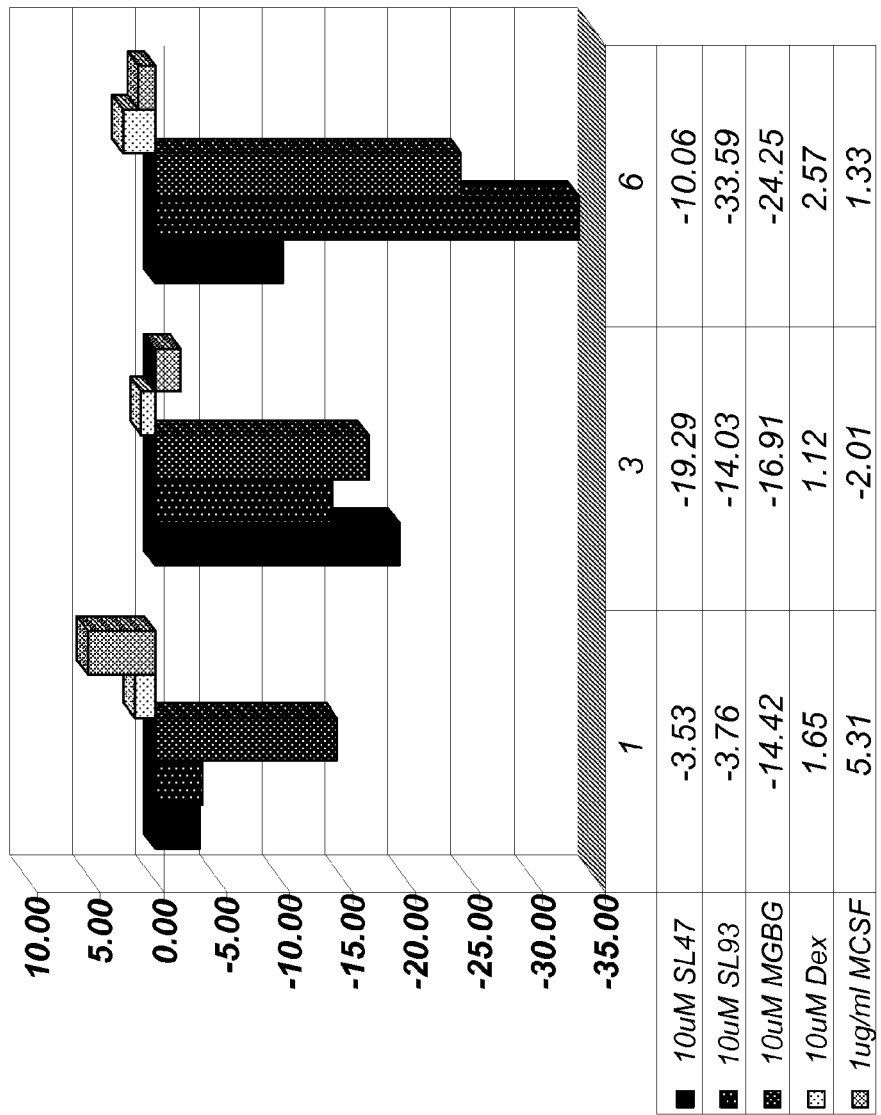
FIG. 12 shows the effect of MGBG on Osteopontin RNA in PBMC cultures.

Polyamine analogs SL47 and SL93 as well as MGBG were compared with dexamethasone and growth factor MCSF in an OPN production inhibition assay. 10 µM of each drug was added to un-stimulated PBMC cultures at time=0 and cells were harvested 1,3, and 6 days later for quantitative OPN RNA and protein production analysis. FIG. 12 shows the effect of (from left to right) SL47, SL93, MGBG, dexamethasone, and MCSF on OPN RNA As seen in FIG. 12, OPN RNA expression was inhibited in a time dependant manner for SL47, SL93, and MGBG. Dexamethasone and MCSF, on the other hand, had no effect on OPN RNA expression.

Figure 13:
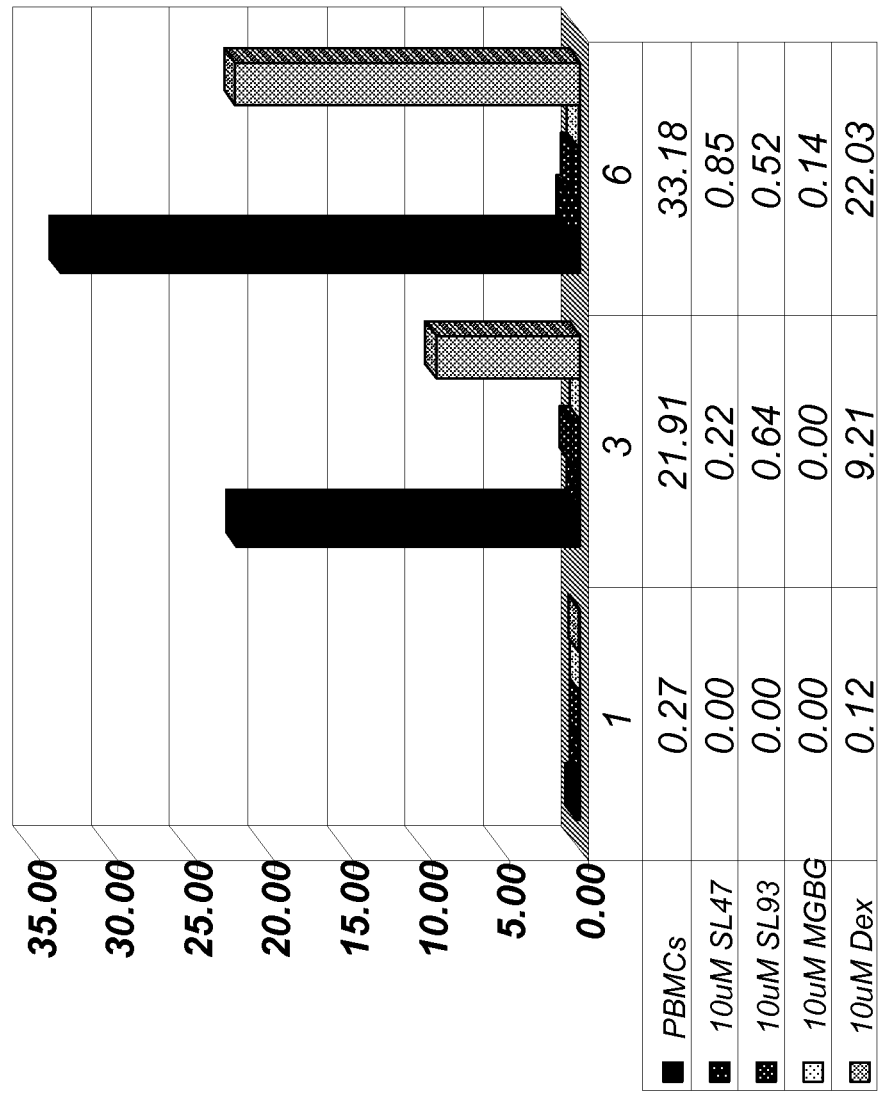
FIG. 13 shows the effect of MGBG on Osteopontin Protein Production in PBMC cultures.

Similar results were observed for OPN production. FIG. 13 shows the quantitative levels of OPN produced in cultures treated with SL47, SL93, MGBG, and dexamethasone as described above. Complete inhibition of OPN protein production was observed in PBMCs treated with MGBG as well as polyamine analogs SL47 and SL93.

All references and publications cited herein are incorporated by reference in their entirety.

It should be noted that there are alternative ways of implementing the present invention. Accordingly, the present embodiments are to be considered as illustrative and not restrictive, and the invention is not to be limited to the details given herein, but may be modified within the scope and equivalents of the appended claims.

The invention claimed is:
1. A method of treating, or alleviating the symptoms of, multiple sclerosis (MS) comprising administering to a subject in need of such treatment an effective amount of MGBG or a salt thereof.

* * * * *

SEQUENCE LISTING

```
<160> NUMBER OF SEQ ID NOS: 62

<210> SEQ ID NO 1
<211> LENGTH: 21
<212> TYPE: DNA
<213> ORGANISM: Homo sapiens

<400> SEQUENCE: 1
agcagcgtcg tcataggtaa t                                             21

<210> SEQ ID NO 2
<211> LENGTH: 21
<212> TYPE: DNA
<213> ORGANISM: Homo sapiens

<400> SEQUENCE: 2
acaggaggat cacttgaggc t                                             21

<210> SEQ ID NO 3
<211> LENGTH: 19
<212> TYPE: DNA
<213> ORGANISM: Homo sapiens

<400> SEQUENCE: 3
ccagcatctg caaagctcc                                                19

<210> SEQ ID NO 4
<211> LENGTH: 20
<212> TYPE: DNA
```

```
<213> ORGANISM: Homo sapiens

<400> SEQUENCE: 4
ttgtacaggg ccaggacctt                                               20

<210> SEQ ID NO 5
<211> LENGTH: 19
<212> TYPE: DNA
<213> ORGANISM: Homo sapiens

<400> SEQUENCE: 5
tgttcggcct cctgctgtt                                                19

<210> SEQ ID NO 6
<211> LENGTH: 21
<212> TYPE: DNA
<213> ORGANISM: Homo sapiens

<400> SEQUENCE: 6
gcttcttttc atcctcctcc a                                             21

<210> SEQ ID NO 7
<211> LENGTH: 21
<212> TYPE: DNA
<213> ORGANISM: Homo sapiens

<400> SEQUENCE: 7
tgctacgaga acttcaccga t                                             21

<210> SEQ ID NO 8
<211> LENGTH: 20
<212> TYPE: DNA
<213> ORGANISM: Homo sapiens

<400> SEQUENCE: 8
gaagcacacc aggaaattga                                               20

<210> SEQ ID NO 9
<211> LENGTH: 20
<212> TYPE: DNA
<213> ORGANISM: Homo sapiens

<400> SEQUENCE: 9
tcttccctga ccttcacgaa                                               20

<210> SEQ ID NO 10
<211> LENGTH: 25
<212> TYPE: DNA
<213> ORGANISM: Homo sapiens

<400> SEQUENCE: 10
catttattaa gcagttacaa tgctg                                         25

<210> SEQ ID NO 11
<211> LENGTH: 25
<212> TYPE: DNA
<213> ORGANISM: Homo sapiens

<400> SEQUENCE: 11
ctacctcata tcagtttgct agcag                                         25

<210> SEQ ID NO 12
<211> LENGTH: 22
```

```
<212> TYPE: DNA
<213> ORGANISM: Homo sapiens

<400> SEQUENCE: 12
cgatctttta gtggtgcctc tt                                              22

<210> SEQ ID NO 13
<211> LENGTH: 25
<212> TYPE: DNA
<213> ORGANISM: Homo sapiens

<400> SEQUENCE: 13
cagtaaagag cttactcctg tagcg                                           25

<210> SEQ ID NO 14
<211> LENGTH: 22
<212> TYPE: DNA
<213> ORGANISM: Homo sapiens

<400> SEQUENCE: 14
aagcctcaga atctgctcca tt                                              22

<210> SEQ ID NO 15
<211> LENGTH: 20
<212> TYPE: DNA
<213> ORGANISM: Homo sapiens

<400> SEQUENCE: 15
gactttccca tgcctttcat                                                 20

<210> SEQ ID NO 16
<211> LENGTH: 21
<212> TYPE: DNA
<213> ORGANISM: Homo sapiens

<400> SEQUENCE: 16
accggaatct gtagtgccct a                                               21

<210> SEQ ID NO 17
<211> LENGTH: 21
<212> TYPE: DNA
<213> ORGANISM: Homo sapiens

<400> SEQUENCE: 17
cgacaggacc agtgcatcta t                                               21

<210> SEQ ID NO 18
<211> LENGTH: 20
<212> TYPE: DNA
<213> ORGANISM: Homo sapiens

<400> SEQUENCE: 18
aactctccca gttgctcctt                                                 20

<210> SEQ ID NO 19
<211> LENGTH: 21
<212> TYPE: DNA
<213> ORGANISM: Homo sapiens

<400> SEQUENCE: 19
cccagctgct gaagagacaa t                                               21

<210> SEQ ID NO 20
```

```
<211> LENGTH: 21
<212> TYPE: DNA
<213> ORGANISM: Homo sapiens

<400> SEQUENCE: 20
atgatcccta cgatggtgca t                                              21

<210> SEQ ID NO 21
<211> LENGTH: 25
<212> TYPE: DNA
<213> ORGANISM: Homo sapiens

<400> SEQUENCE: 21
ggatagctgt tgtttcagag aaagg                                          25

<210> SEQ ID NO 22
<211> LENGTH: 25
<212> TYPE: DNA
<213> ORGANISM: Homo sapiens

<400> SEQUENCE: 22
cttctcacaa atactatatg agggc                                          25

<210> SEQ ID NO 23
<211> LENGTH: 21
<212> TYPE: DNA
<213> ORGANISM: Homo sapiens

<400> SEQUENCE: 23
aacacgacca tcgtagggtg a                                              21

<210> SEQ ID NO 24
<211> LENGTH: 20
<212> TYPE: DNA
<213> ORGANISM: Homo sapiens

<400> SEQUENCE: 24
tttgaggtga tggtgggata                                                20

<210> SEQ ID NO 25
<211> LENGTH: 20
<212> TYPE: DNA
<213> ORGANISM: Homo sapiens

<400> SEQUENCE: 25
caccgatggc catgtaaata                                                20

<210> SEQ ID NO 26
<211> LENGTH: 20
<212> TYPE: DNA
<213> ORGANISM: Homo sapiens

<400> SEQUENCE: 26
tgtccaggaa aagccatctt                                                20

<210> SEQ ID NO 27
<211> LENGTH: 20
<212> TYPE: DNA
<213> ORGANISM: Homo sapiens

<400> SEQUENCE: 27
tggaacaggt gcctaaagga                                                20
```

```
<210> SEQ ID NO 28
<211> LENGTH: 19
<212> TYPE: DNA
<213> ORGANISM: Homo sapiens

<400> SEQUENCE: 28
acagggtcga acgtgcaca                                              19

<210> SEQ ID NO 29
<211> LENGTH: 22
<212> TYPE: DNA
<213> ORGANISM: Homo sapiens

<400> SEQUENCE: 29
tgaatgagga gttctggtac ct                                          22

<210> SEQ ID NO 30
<211> LENGTH: 24
<212> TYPE: DNA
<213> ORGANISM: Homo sapiens

<400> SEQUENCE: 30
agtcaagcca cagactaggt gtaa                                        24

<210> SEQ ID NO 31
<211> LENGTH: 21
<212> TYPE: DNA
<213> ORGANISM: Homo sapiens

<400> SEQUENCE: 31
acacagattt gagctcagcc c                                           21

<210> SEQ ID NO 32
<211> LENGTH: 20
<212> TYPE: DNA
<213> ORGANISM: Homo sapiens

<400> SEQUENCE: 32
atgtttggct ccttggtgat                                             20

<210> SEQ ID NO 33
<211> LENGTH: 22
<212> TYPE: DNA
<213> ORGANISM: Homo sapiens

<400> SEQUENCE: 33
aggtattaag cccagtgcct aa                                          22

<210> SEQ ID NO 34
<211> LENGTH: 25
<212> TYPE: DNA
<213> ORGANISM: Homo sapiens

<400> SEQUENCE: 34
gaaaattatg tcttttgtgg gaaca                                       25

<210> SEQ ID NO 35
<211> LENGTH: 21
<212> TYPE: DNA
<213> ORGANISM: Homo sapiens

<400> SEQUENCE: 35
tttctgagat gaagtcgagg g                                           21
```

<210> SEQ ID NO 36
<211> LENGTH: 21
<212> TYPE: DNA
<213> ORGANISM: Homo sapiens

<400> SEQUENCE: 36
tctgcttgga gcacttaaac a                                             21

<210> SEQ ID NO 37
<211> LENGTH: 21
<212> TYPE: DNA
<213> ORGANISM: Homo sapiens

<400> SEQUENCE: 37
aattgtgttg ctcctggagg a                                             21

<210> SEQ ID NO 38
<211> LENGTH: 20
<212> TYPE: DNA
<213> ORGANISM: Homo sapiens

<400> SEQUENCE: 38
caatgccatt tcctttccca                                               20

<210> SEQ ID NO 39
<211> LENGTH: 23
<212> TYPE: DNA
<213> ORGANISM: Homo sapiens

<400> SEQUENCE: 39
ttgcccatgg tttccagaac aag                                           23

<210> SEQ ID NO 40
<211> LENGTH: 23
<212> TYPE: DNA
<213> ORGANISM: Homo sapiens

<400> SEQUENCE: 40 gggattttttt ccttgtgttt tca                                          23

<210> SEQ ID NO 41
<211> LENGTH: 19
<212> TYPE: DNA
<213> ORGANISM: Homo sapiens

<400> SEQUENCE: 41
agtatggatc tcaggcggt                                                19

<210> SEQ ID NO 42
<211> LENGTH: 19
<212> TYPE: DNA
<213> ORGANISM: Homo sapiens

<400> SEQUENCE: 42
catcggttgt aacattacc                                                19

<210> SEQ ID NO 43
<211> LENGTH: 21
<212> TYPE: DNA
<213> ORGANISM: Homo sapiens

<400> SEQUENCE: 43
atggccttag ctcttagcca a                                             21

<210> SEQ ID NO 44
<211> LENGTH: 20
<212> TYPE: DNA
<213> ORGANISM: Homo sapiens

<400> SEQUENCE: 44
gctcttgcgc tttgacttta                                           20

<210> SEQ ID NO 45
<211> LENGTH: 25
<212> TYPE: DNA
<213> ORGANISM: Homo sapiens

<400> SEQUENCE: 45
agaccttcta tctgaggaac aacca                                     25

<210> SEQ ID NO 46
<211> LENGTH: 21
<212> TYPE: DNA
<213> ORGANISM: Homo sapiens

<400> SEQUENCE: 46
ttgtcctgct ttctgttctc g                                         21

<210> SEQ ID NO 47
<211> LENGTH: 21
<212> TYPE: DNA
<213> ORGANISM: Homo sapiens

<400> SEQUENCE: 47
tccactgggc acagaactta t                                         21

<210> SEQ ID NO 48
<211> LENGTH: 20
<212> TYPE: DNA
<213> ORGANISM: Homo sapiens

<400> SEQUENCE: 48
tctggctctg aaacaaagga                                           20

<210> SEQ ID NO 49
<211> LENGTH: 21
<212> TYPE: DNA
<213> ORGANISM: Homo sapiens

<400> SEQUENCE: 49
tgccttctgc ttttaagttg c                                         21

<210> SEQ ID NO 50
<211> LENGTH: 20
<212> TYPE: DNA
<213> ORGANISM: Homo sapiens

<400> SEQUENCE: 50
gatgaagggg ttcccataaa                                           20

<210> SEQ ID NO 51
<211> LENGTH: 22
<212> TYPE: DNA
<213> ORGANISM: Homo sapiens

<400> SEQUENCE: 51
agccacaagc agtccagatt at                                    22

<210> SEQ ID NO 52
<211> LENGTH: 23
<212> TYPE: DNA
<213> ORGANISM: Homo sapiens

<400> SEQUENCE: 52
ttgacctcag aagatgcact atc                                   23

<210> SEQ ID NO 53
<211> LENGTH: 22
<212> TYPE: DNA
<213> ORGANISM: Homo sapiens

<400> SEQUENCE: 53
actctgggtt atactggtgc ga                                    22

<210> SEQ ID NO 54
<211> LENGTH: 23
<212> TYPE: DNA
<213> ORGANISM: Homo sapiens

<400> SEQUENCE: 54
ccaaagagat ttctaaatcc cac                                   23

<210> SEQ ID NO 55
<211> LENGTH: 21
<212> TYPE: DNA
<213> ORGANISM: Homo sapiens

<400> SEQUENCE: 55
tccctgtgaa tgacagcatg t                                     21

<210> SEQ ID NO 56
<211> LENGTH: 21
<212> TYPE: DNA
<213> ORGANISM: Homo sapiens

<400> SEQUENCE: 56
aaactgcaag aaatctgagc c                                     21

<210> SEQ ID NO 57
<211> LENGTH: 22
<212> TYPE: DNA
<213> ORGANISM: Homo sapiens

<400> SEQUENCE: 57
cagtcaggca gaagtatgca aa                                    22

<210> SEQ ID NO 58
<211> LENGTH: 24
<212> TYPE: DNA
<213> ORGANISM: Homo sapiens

<400> SEQUENCE: 58 tcccttttgtc ctagaaagtt gagg                                 24

<210> SEQ ID NO 59
<211> LENGTH: 19
<212> TYPE: DNA
<213> ORGANISM: Homo sapiens

<400> SEQUENCE: 59
gctaccacac cctggaaga                                          19

<210> SEQ ID NO 60
<211> LENGTH: 21
<212> TYPE: DNA
<213> ORGANISM: Homo sapiens

<400> SEQUENCE: 60
ccgtttggtc atctggtaat c                                       21

<210> SEQ ID NO 61
<211> LENGTH: 21
<212> TYPE: DNA
<213> ORGANISM: Homo sapiens

<400> SEQUENCE: 61
aacagagagg gatgcttgga t                                       21

<210> SEQ ID NO 62
<211> LENGTH: 20
<212> TYPE: DNA
<213> ORGANISM: Homo sapiens

<400> SEQUENCE: 62
caccaaggga aagggatgat                                         20